United States Patent [19]
Haseloff et al.

[11] Patent Number: 6,015,794
[45] Date of Patent: *Jan. 18, 2000

[54] TRANS-SPLICING RIBOZYMES

[75] Inventors: James Haseloff, Cambridge; Howard M. Goodman, Newton, both of Mass.

[73] Assignee: The General Hospital Corporation, Boston, Mass.

[ * ] Notice: This patent is subject to a terminal disclaimer.

[21] Appl. No.: 08/470,349

[22] Filed: Jun. 6, 1995

Related U.S. Application Data

[62] Division of application No. 08/090,192, Nov. 17, 1993, and a continuation of application No. PCT/US92/00278, Jan. 16, 1992, which is a continuation-in-part of application No. 07/642,333, Jan. 17, 1991, abandoned.

[51] Int. Cl.⁷ ............................. C12Q 1/68; C07H 21/04; A61K 48/00
[52] U.S. Cl. ............................. 514/44; 435/6; 435/91.31; 435/91.33; 435/252.3; 435/320.1; 435/325; 435/375; 435/410; 536/23.1; 536/23.2; 536/24.5; 800/205
[58] Field of Search ......................... 435/6, 91.31, 320.1, 435/240.1, 240.2, 252.3; 514/44; 536/23.2, 23.1, 24.5

[56] References Cited

U.S. PATENT DOCUMENTS 5,037,746   8/1991   Cech et al. .................................. 435/91

FOREIGN PATENT DOCUMENTS

| | | |
|---|---|---|
| 0 240 208 | 10/1987 | European Pat. Off. . |
| 0 321 201 | 6/1989 | European Pat. Off. . |
| WO 87/03451 | 6/1987 | WIPO . |
| WO 88/04300 | 6/1988 | WIPO . |
| WO 89/05852 | 6/1989 | WIPO . |
| WO 90/11364 | 10/1990 | WIPO . |
| WO 90/13654 | 11/1990 | WIPO . |
| WO 91/06302 | 5/1991 | WIPO . |
| WO 91/14699 | 10/1991 | WIPO . |
| WO 92/13089 | 8/1992 | WIPO . |

OTHER PUBLICATIONS

San, H. et al., Safety and Short Term Toxicity of a Novel and Cationic Formulation for Human Gene Therapy, Human Gene Therapy, 781–788, Dec. 1993.
Christoffersen, R. et al., Ribozymes as Human Therapeutic Agents, Journal of Medicinal Chemistry, 2023–2037, Nov. 1994.
Stull, R. et al., Antigene, Ribozyme, and Aptomer Nucleic Acid Drugs: Progress and Prospects, Pharmaceuticals Research, 1995.
Agabian, N., "Trans Splicing of Nuclear Pre–mRNAS," *Cell* 61(7):1157–1160 (Jun. 1990).
Barinaga, M., "Ribozymes: Killing the Messenger," *Science* 262:1512–1514 (1993).
Been, M.D., et al., "One binding site determines sequence specificity of *Tetrahymena* pre–mRNA self splicing, trans–splicing, and RNA enzyme activity," *Cell* 47(2):207–216 (1986).
Been, M.D., et al., "Selection of Circularization Sites in a Group I IVS RNA Requires Multiple Alignments of an Internal Template–Like Sequence," *Cell* 50:951–961 (1987).
Brand, A., et al., "A General Method for Directed Gene Expression in Drosophila," Presented at The Genome Conference, 13th Annual Conference on the Organisation and Expression of the Genome, Victoria, Australia, Feb. 18–22, 1991, SYM–15–2.
Cech, T.R., "Self–Splicing of Group I Introns," *Ann. Rev. Biochem.* 59: 543–568 (Jul. 1990).
Cech, T.R., "Conserved sequences and structures of group I introns: building an active site for RNA catalysis—a review," *Gene* 73:259–271 (1988).
Chuat, J.C., et al., "Can Ribozymes Be Used to Regulate Procaryote Gene Expression?," *Biochem. Biophys. Res. Commun.* 162(3):1025–1029 (1989).
Cotten, M., et al., "Ribozyme Mediated Destruction of RNA in vivo," *EMBO J.* 8(12):3861–3866 (1989).
Cotten, M., "The in vivo application of ribozymes," *Trends Biotech.* 8(7):174–178 (Jul. 1990).
Doudna, J.A., et al., "RNA structure, not sequence, determines the 5' splice–site specificity of a group I intron," *Proc. Natl. Acad. Sci.* 86:7402–7406 (1989).
Evans, G.A., "Dissecting mouse development with toxigenics," *Genes and Develop.* 3:259–263 (1982).
Flanegan, J.B., et al., "Tetrahymena Ribozyme Catalyzes Trans–Splicing of Model Oligoribonucleotide Substrates," *J. Cell Biochem. Supp.* 12D:28 N202 (1988), Presented at the Symposium of the Molecular Biology of RNA Held at the 17th Annual UCLA Symposia on Molecular and Cellular Biology, Keystone, CO (Apr. 1988).
Garriga, G., et al., "Mechanism of recognition of the 5' splice site in self–splicing group I introns," *Nature* 322:86–89 (1986).
Haseloff, J., et al., "Simple RNA enzymes with new and highly specific endoribonuclease activities," *Nature* 334:585–591 (1988).
Haseloff, J., et al.,"Design of Ribozymes for Trans–Splicing," Presented at The Genome Conference, 13th Annual Conference on the Organisation and Expression of the Genome, Victoria, Australia, Feb. 18–22, 1991, SYM–8–1.
Heus, H.A., et al., "Sequence–dependent structural variations of hammerhead RNA enzymes," *Nucl. Acids Res.* 18(5):1103–1108 (Mar. 1990).
Hirsh, D., et al., "Trans–Splicing and SL RNAs in *C. elegans*," *Mol. Biol. Rep.* 14(2/3):115 (Mar. 1990).

(List continued on next page.)

*Primary Examiner*—John L. LeGuyader
*Attorney, Agent, or Firm*—Sterne, Kessler, Goldstein & Fox P.L.L.C.

[57] ABSTRACT

The design of new ribozymes capable of self-catalyzed trans-splicing which are based upon the catalytic core of a Group I intron are described. Using this design, it is possible to construct ribozymes capable of efficiently splicing a new 3' exon sequence into any chosen target RNA sequence in a highly precise manner. Inactive pro-ribozyme forms are also described.

40 Claims, 20 Drawing Sheets

OTHER PUBLICATIONS

Hutchins, C.J., et al., "Self–cleavage of plus and minus RNA transcripts of avocado sunblotch viroid," *Nucl. Acids. Res.* 14(9):3627–3640 (1986).

Joyce, G.F., "Amplification, mutation and selection of catalytic RNA," *Gene* 82:83–87 (1989).

Kan, N.C., et al., "The intervening sequence of the ribosomal RNA gene is highly conserved between Two *Tetrahymena* species," *Nucl. Acids. Res.* 10(9):2809–2822 (1982).

Keese, P., et al., "The Structure of Viroids and Virusoids," in: *Viroids and Viroid–like Pathogens*, J.S. Semancik, ed., Boca Raton, FL: CRC Press, pp. 1–47 (1987).

Koizumi, M., et al., "Construction of a series of several self–cleaving RNA duplexes using synthetic 21–mers," *FEBS Letts.* 228(2):228–230 (1988).

Koizumi, M., et al., "Cleavage of specific sites of RNA by designed ribozymes," *FEBS Letts.* 239(2):285–288 (1988).

Mariani, C., et al., "Induction of male sterility in plants by a chimaeric ribonuclease gene," *Nature* 347 (6295):737–741 (Oct. 1990).

Maxwell, I.H., et al., "Regulated Expression of a Diphtheria Toxin A–Chain Gene Transfected into Human Cells: Possible Strategy for Inducing Cancer Cell Suicide," *Cancer Research* 46:4660–4664 (1986).

Michel, F., et al., "The guanosine binding site of the Tetrahymena ribozyme," *Nature* 342:391–395 (1989).

Rezaian, M.A., et al., "Nucleotide sequence of cucumber mosaic virus RNA 1—Presence of a sequence complementary to part of the viral satellite RNA and homologies with other viral RNAs," *Eur. J. Biochem.* 150:331–339 (1985).

Riedel, C.J., et al., "Diphtheria toxin mutant selectively kills cerebellar purkinje neurons," *Proc. Natl. Acad. Sci. USA* 87:5051–5055 (Jul. 1990).

Salvo, J.L.G., et al., "Deletion–tolerance and Trans–splicing of the Bacteriophage T4 td Intron," *J. Mol. Biol.* 211(3):537–549 (Feb. 1990).

Sarver, N., et al., "Ribozymes as Potential Anti–HIV–1 Therapeutic Agents," *Science* 247(4947):1222–1225 (Mar. 1990).

Suh, E.R., et al., "Base Pairing between the 3' Exon and an Internal Guide Sequence Increases 3' Splice Site Specificity in the Tetrahymena Self–Splicing rRNA Intron," *Mol. Cell. Biol.* 10(6):2960–2965 (Jun. 1990).

Sullenger, B.A., et al., "Ribozyme–mediated repair of defective mRNA by targeted trans–splicing," *Nature* 371:619–622 (1994).

Szostak, J.W., "Enzymatic activity of the conserved core of a group I self–splicing intron," *Nature* 322:83–86 (1986).

Taira, K., et al., "Construction of a novel artificial–ribozyme–releasing plasmid," *Protein Engineering* 3(8):733–737 (Aug. 1990).

Waring, R.B., et al., "The Tetrahymena rRNA Intron Self–Splices in *E. coli*: In Vivo Evidence for the Importance of Key Base–Paired Regions of RNA for RNA Enzyme Function," *Cell* 40:371–380 (1985).

Winter, A.J., et al., "The mechanism of Group I self–splicing: an internal guide sequence can be provided in Trans," *EMBO J.* 9(6):1923–1928 (Jun. 1990).

Yagi, T., et al., "Homologous Recombination at c–fyn locus of mouse embryonic stem cells with use of diphtheria toxin A–fragment gene in negative selection," *Proc. Natl. Acad. Sci. USA* 87:9918–9922 (Dec. 1990).

Zaug, A.J., et al., "Intervening Sequence RNA of Tetrahymena Is an Enzyme," *Science* 231:470–475 (1986).

1. GUANOSINE-MEDIATED CLEAVAGE OF 5' SPLICE SITE.
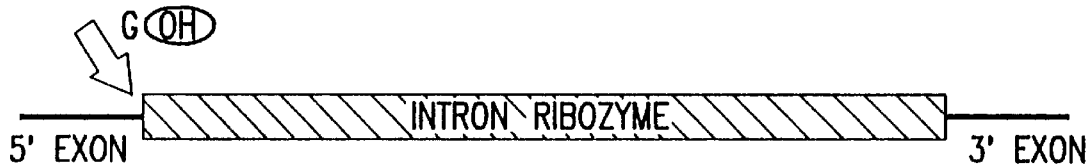
2. CLEAVAGE OF 3' SPLICE SITE.
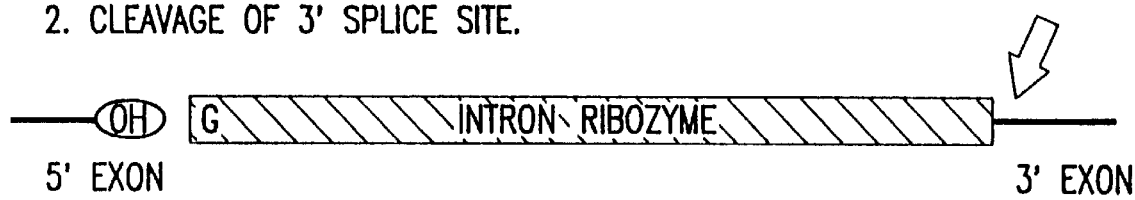
3. LIGATION OF EXON SEGMENTS.
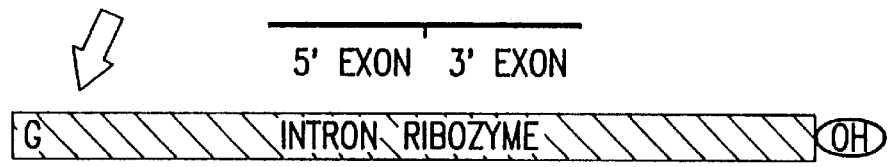
4. CIRCULARIZATION OF INTRON.
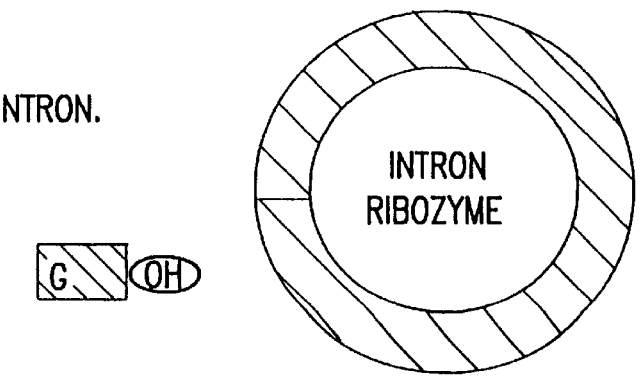
FIG.1

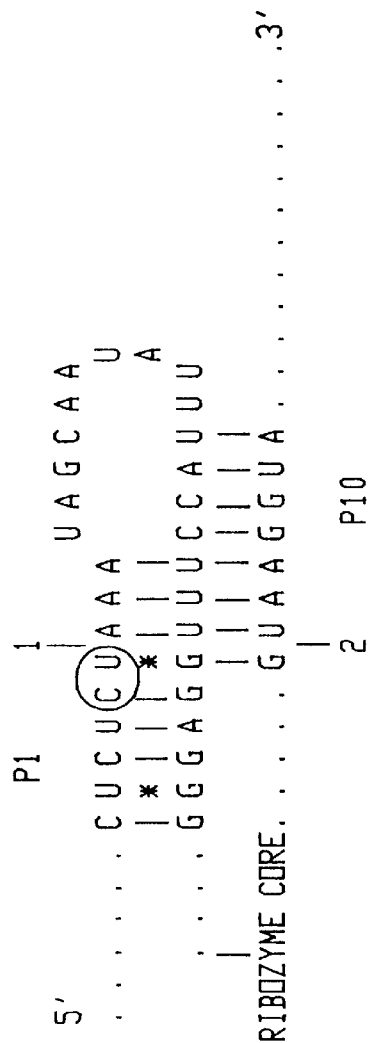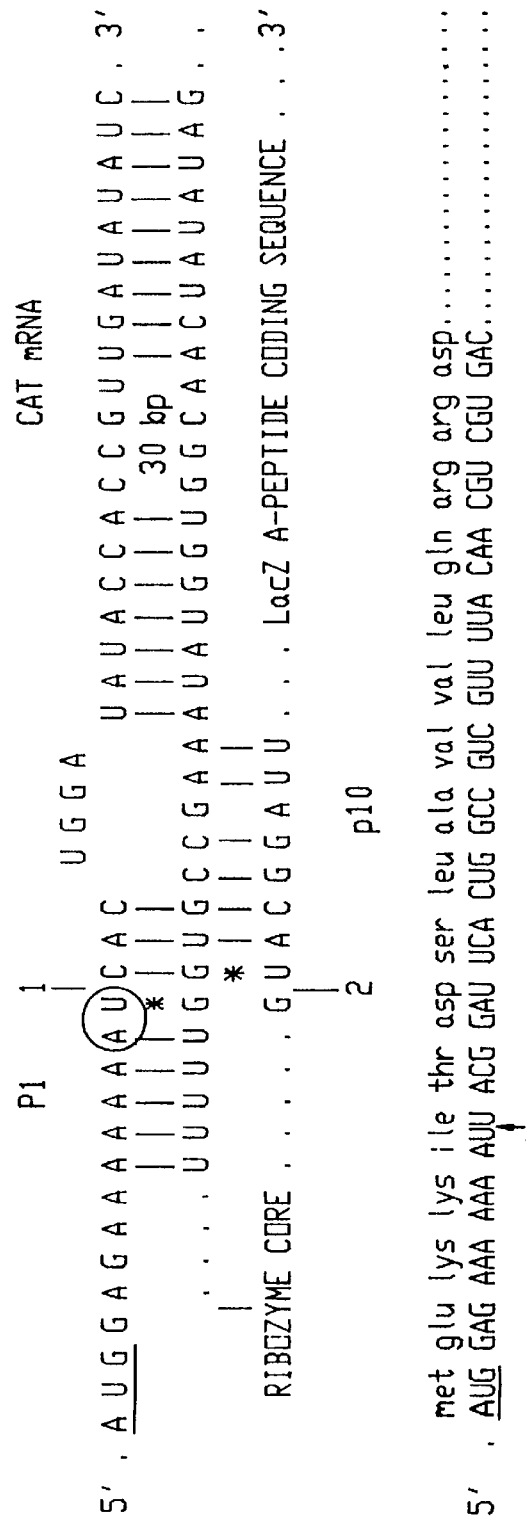
FIG.3A

```
            10         20         30         40         50         60
            |          |          |          |          |          |
  1  GGGAGACCGG AAGCTTCTTT ACGATGCCAT TGGATATATAT CAACGGTGGT ATAAAGCCGT   60
 61  GGTTTTAAAA AGTTATCAGG CATGCACCTG GTAGCTAGTC TTTAAACCAA TAGATTGCAT  120
121  CGGTTTAAAA GGCAAGACCG TCAAATTGCC GGAAAGGGGT CAACAGCCGT TCAGTACCAA  180
181  GTCTCAGGGG AAACTTTGAG ATGGCCTTGC AAAGGGTATG GTAATAAGCT GACGGACATG  240
241  GTCCTAACCA CGCAGCCAAG TCCTAAGTCA ACAGATCTTC TGTTGATATG GATGCAGTTC  300
301  ACAGACTAAA TGTCGGTCGG GGAAGATGTA TTCTTCTCAT AAGATATAGT CGGACCCTCT  360
361  CTTAATGGGA GCTAGCGGAT GAAGTGATGC AACACTGGAG CCGCTGGGAA CTAATTTGTA  420
421  TGCGAAAGTA TATTGATTAG TTTTGGAGTA CTCGTACGGA TTCACTGGCC GTCGTTTTAC  480
481  AACGTCGTGA CTGGGAAAAC CCTGGCGTTA CCCAACTTAA TCGCCTTGCA GCACATCCCC  540
541  CTTTCGCCAG CTGGCGTAAT AGCGAAGAGG CCCGCACCGA TCGCCCTTCC CAACAGTTGC  600
601  GCAGCCTGAA TGGAAATTGT AAG                                         623
            |          |          |          |          |          |
            10         20         30         40         50         60
```

FIG. 3B

CMV isolates.

```
                                               1                 2
                                               |                 |
WD   UUUGCGUCU......UAGUGUGCCU AUG GAC AAA U.CU GGA U.CU CCC AAU GCU AGU
Q    UUUGCGUCUCAG......UGUGCCU AUG GAC AAA U.CU GGA U.CU CCC AAU GCU AGU
Fny  UUUGUGUCGUAGAAUUGAGUCGAGUC AUG GAC AAA U.CU GGA U.CU ACC AGU GCU GGU
M    UUUGUGUCGUAGAAUUGAGUCGAGUC AUG GAU AAA U.CU GAA U.CA ACC AGU GCU GGU
I    UUUGUGUCGUAGAAUUGAGUCGAGUC AUG GAC AAA U.CU GAA U.CA ACC AGU GCU GGU
O    UUUGUGUCGUAGAAUUGAGUCGAGUC AUG GAC AAA U.CU GAA U.CA ACC AGU GCU GGU
Y    UUUACGUCGUAGAAUUGAGUCGAGUC AUG GAC AAA U.CU GAA U.CA ACC AGU GCU GGU
D    UUUGUGUCGUAGAAUUGAGUCGAGUC AUG GAC AAA U.CU GAA U.CA ACC AGU GCU GGU
C    UUUGUGUCGUAGAAUUGAGUCGAGUC AUG GAC AAA U.CU GAA U.CA ACC AGU GCU GGU
5'                                                                    3'
```

Ribozyme 1

```
5'AAUUUUGUGUCGUAGAAUUGAGUCGAGUCAUGGACAAAU.CUGAAUCAACCAGUGCUGCA 3'
                                   ||||*  ||||       |||||||||| (41 bp)
                          .......UGUUUG  GACUACUAUGGUUACGA  ... 5'
                                          *||||||||****
                RIBOZYME CORE........G.UUGAUGAUAGGUACCUCGAUGAUGUUGUUGAU.... 3'
                                    |
                                    1
                met asp lys phe asp asp arg tyr leu asp asp val ser....
                AUG GAC AAA UUU GAU GAU AGG UAC CUC GAU GAU GUU UCU...3'
```

Ribozyme 2

```
5'AAUUUUGUGUCGUAGAAUUGAGUCGAGUCAUGGACAAAU.CAACCAGUGCUGCA 3'
                                   ||||* |||    |||  (46 bp)
                            .GACUUG  GUUCCUACCGA  ... 5'
                                      *||||*|||
                RIBOZYME CORE........G.UAAGGGUGGGGUACCUCGAUGAUGUUGUUGAU.... 3'
                                    |
                                    2
                met asp lys ser glu leu arg val gly tyr leu asp asp....
                AUG GAC AAA UCU GAA UUA AGG GUG GGG UAC CUC GAU GAU...3'
```

TRANSLATION OF 3' 'EXONS'

```
                5'                                                                                        3'
Rz-DTA met        TCTCGATGATGTTGTTGATTCTTCTAAATCTTTTGTG ATG GAA AAC TTT TCT TCG TAC CAC GGG ACT AAA ... ... ...
                                                        met glu asn phe ser ser tyr his gly thr lys 5'                                                                                        3'
Rz-DTA ile        TCTCGATGATGTTGTTGATTCTTCTAAATCTTTTGTG ATT GAA AAC TTT TCT TCG TAC CAC GGG ACT AAA ... ... ...
                                                        ile 5'                                                                                        3'
Rz-DTA leu        TCTCGATGATGTTGTTGATTCTTCTAAATCTTTTGTG TTG GAA AAC TTT TCT TCG TAC CAC GGG ACT AAA ... ... ...
                                                        leu
```

FIG.6A

```
                  10         20         30         40         50         60
   1  GTCGACCTTT TTAAGTCGGC AAATATCGCA TGTTTGTTCG ATAGACATCG AGTGGCTTCA   60
  61  AAAGTTATCA GGCATGCACC TGGTAGCTAG TCTTTAAACC AATAGATTGC ATCGGTTTAA  120
 121  AAGGCAAGAC CGTCAAATTG CGGGAAAGGG GTCAACAGCC GTTCAGTACC AAGTCTCAGG  180
 181  GGAAACTTTG AGATGGCCTT GCAAAGGGTA CTGACGGACA TGGTCCTAAC  240
 241  CACGCAGCCA AGTCCTAAGT CAACAGATCT TCTGTTGATA TGGATGCAGT TCACAGACTA  300
 301  AATGTCGGTC GGGGAAGATG TATTCTTCTC ATAAGATATA GTCGGACCTC TCCTTAATGG  360
 361  GAGCTAGCGG ATGAAGTGAT GCAACACTGG AGCCGCTGGG AACTAATTTG TATGCGAAAG  420
 421  TATATTGATT AGTTTGGAG TACTCGTCTC GATGATGTTG TTGATTCTTC TAAATCTTTT  480
 481  GTGATTGAAA ACTTTTCTTC GTACCACGGG ACTAAACCTG GTTATGTAGA TTCCATTCAA  540
 541  AAAGGTATAC AAAAGCCAAA ATCTGGTACA CAAGGAAATT ATGACGATGA TTGGAAAGGG  600
 601  TTTTATAGTA CCGACAATAA ATACGACGCT GCGGGATACT CTGTAGATAA TGAAAACCCG  660
 661  CTCTCTGGAA AAGCTGGAGG CGTGGTCAAA GTGACGTATC CAGGACTGAC GAAGGTTCTC  720
 721  GCACTAAAAG TGGATAAATGC CGAAACTATT AAGAAAGAGT TAGGTTTAAG TCTCACTGAA  780
 781  CCGTTGATGG AGCAAGTCGG AACGGAAGAG TTTATCAAAA GGTTCGGTGA TGGTGCTTCG  840
 841  CGTGTAGTGC TCAGCCTTCC CTTCGCTGAG GGGAGTTCTA GCGTTGAATA TATTAATAAC  900
 901  TGGGAACAGG AAGCCGTT ATGCGATGTA CGAAAGCCT GTGCAGGAAA CCGTGGAAAA  960
 961  CGTGGCCAAG ATGCGATGTA GAGTATATG GCTCAAGCCT GTGCAGGAAA TCGTGTCAGG 1020
1021  CGATCTTTGT GACTCGAG                                               1038
                  10         20         30         40         50         60
```

FIG. 6B

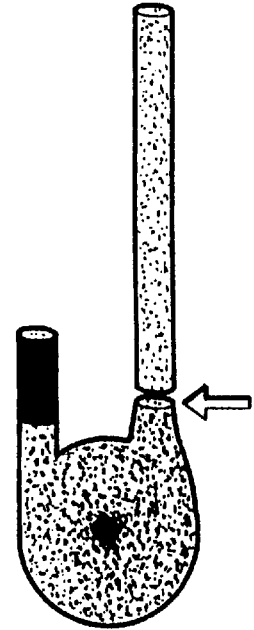
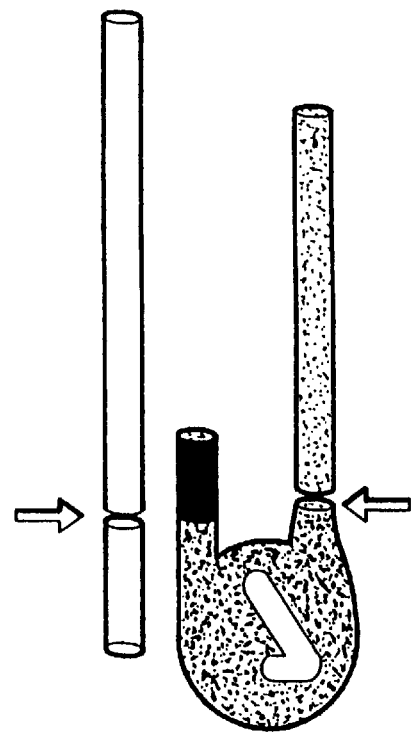
FIG.7A FIG.7B FIG.7D
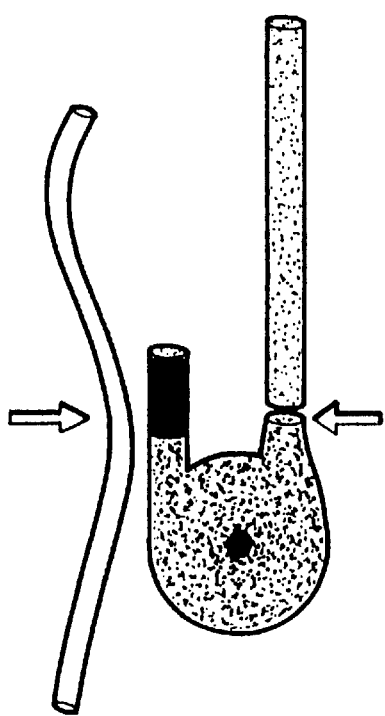
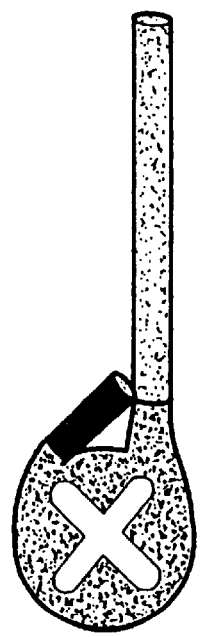
FIG.7C

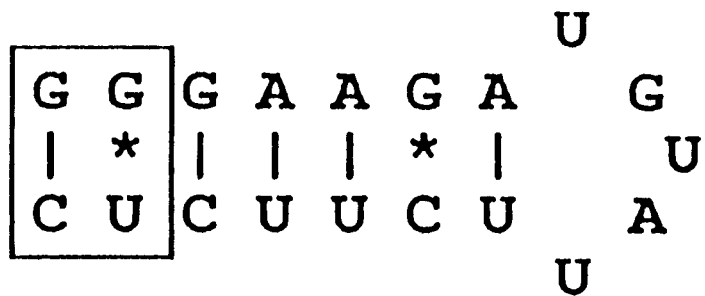
13 nt
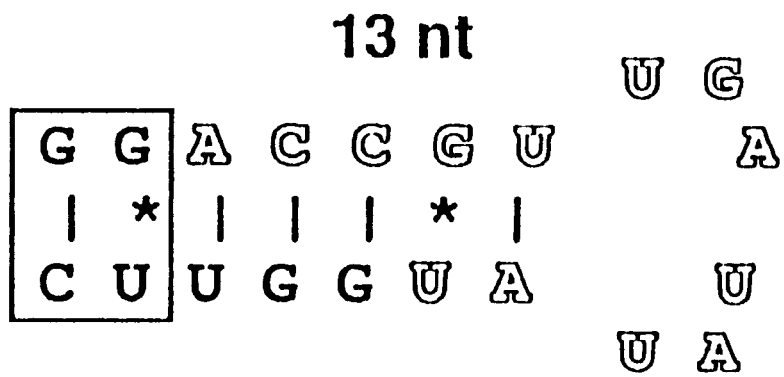
18 nt
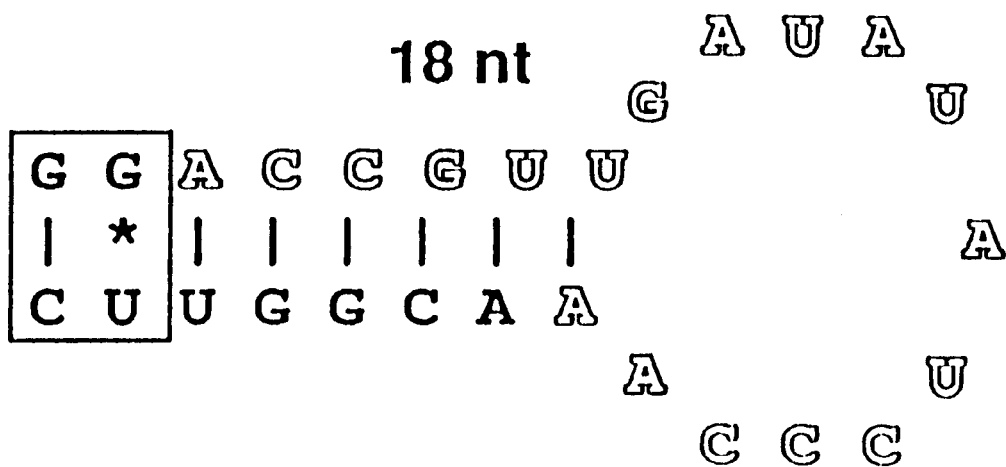
N = complementary to "anti-sense"
FIG. 8C

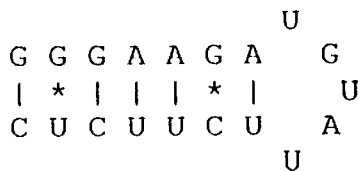
Wild-type
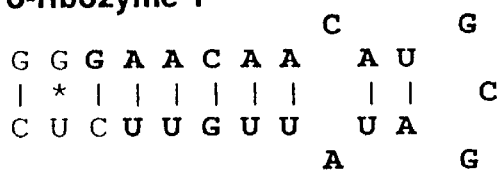
GAL4-DTA pro-ribozyme 1    20 nt
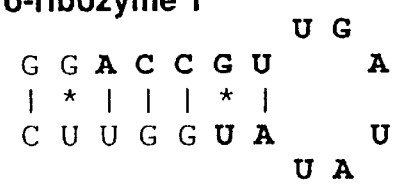
CAT-LacZ pro-ribozyme 1    13 nt
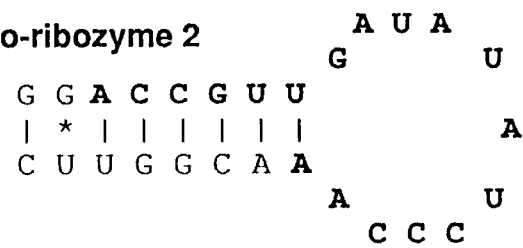
CAT-LacZ pro-ribozyme 2    18 nt
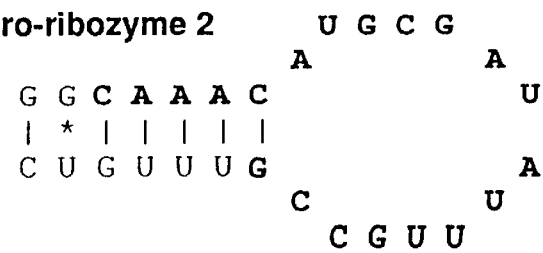
GAL4-DTA pro-ribozyme 2    20 nt
INCREASING STABILITY
N = complementary to ribozyme "anti-sense"
FIG. 12

TRANS-SPLICING RIBOZYMES

CROSS REFERENCES TO RELATED APPLICATIONS

This application is a division of application Ser. No. 08/090,192, filed Nov. 17, 1993, which is the U.S. National Phase of PCT application no. PCT/US92/00278, filed Jan. 16, 1992, which is a continuation-in-part of application Ser. No. 07/642,333, filed Jan. 17, 1991, now abandoned.

FIELD OF THE INVENTION

The present invention is directed to novel ribozymes capable of trans-splicing reactions.

BRIEF DESCRIPTION OF THE BACKGROUND ART

I. Group I Introns

RNA molecules with catalytic activity are called ribozymes or RNA enzymes (Cech, T. R., *Ann. Rev. Biochem.* 59:543–568 (1990). The *Tetrahymena thermophila* precursor rRNA contains an intron (a ribozyme) capable of catalyzing its own excision. This ribozyme is one of a class of structurally related Group I introns.

The splicing activity of the modified *T. therrmophila* intron requires the presence of a guanosine cofactor and a divalent cation, either $Mg^{++}$ or $Mn^{++}$, and occurs via two sequential transesterification reactions (FIG. 1). First, a free guanosine is bound to the ribozyme and its 3' hydroxyl group is positioned to attack the phosphorus atom at the 5' splice site. The guanosine is covalently attached to the intron sequence and the 5' exon is released. Second, the phosphodiester bond located at the 3' splice site undergoes attack from the newly freed 3' hydroxyl group of the 5' exon, resulting in production of the ligated exon sequences. The excised intron subsequently undergoes a series of transesterification reactions, involving its 3' hydroxyl group and internal sequences, resulting in the formation of shortened circular forms.

These successive reactions are chemically similar and appear to occur at a single active site. The reactions of self-splicing are characterized by the formation of alternative RNA structures as differing RNA chains are each brought to form similar conformations around the highly conserved intron. Splicing requires the alignment of the intron-exon junctions across a complementary sequence termed the "internal guide sequence" or IGS.

The first cleavage at the 5' splice site requires the formation of a base-paired helix (P1) between the IGS and sequences adjacent the splice site. The presence of a U:G "wobble" base-pair within this helix defines the phosphodiester bond that will be broken in the catalytic reaction of the ribozyme. After cleavage of this bond, a portion the P1 helix is displaced and a new helix, P10, is formed due to complementarity between the IGS and sequences adjacent the 3' splice site. An invariant guanosine residue precedes the phosphodiester at the 3' splice site, similar to the portion of the P1 sequence that it is displacing. Thus, ligation of the exons occurs in a reverse of the first cleavage reaction but where new exon sequences have been substituted for those of the intron. It may be noted that intron circularization reactions subsequent to exon ligation also involve base-pairing of 5' sequences across the IGS, and attack mediated by the 3' hydroxyl group of the intron'terminal guanine residue (Been, M. D. et al., "Selection Of Circularization Sites In A Group I IVS RNA Requires Multiple Alignments Of An Internal Template-Like Sequence," *Cell* 50:951 (1987)).

II. Catalytic Activities

In order to better define the structural and catalytic properties of the Group I introns, exon sequences have been stripped from the "core" of the *T. thermophila* intron. Cech, T. R. et al., WO 88/04300, describes at least three catalytic activities possessed by the Tetrahymena intron ribozyme: (1) a dephosphorylating activity, capable of removing the 3' terminal phosphate of RNA in a sequence-specific manner, (2) an RNA polymerase activity (nucleotidyl transferase), capable of catalyzing the conversion of oligoribonucleotides to polyribonucleotides, and (3) a sequence-specific endoribonuclease activity.

Isolated ribozyme activities can interact with substrate RNAs in trans, and these interactions characterized. For example, when truncated forms of the intron are incubated with sequences corresponding to the 5' splice junction, the site undergoes guanosine-dependent cleavage in mimicry of the first step in splicing. The substrate and endoribonucleolytic intron RNAs base-pair to form helix P1, and cleavage occurs after a U:G base-pair at the 4th–6th position. Phylogenetic comparisons and mutational analyses indicate that the nature of the sequences immediately adjacent the conserved uracil residue at the 5' splice site are unimportant for catalysis, provided the base-pairing of helix P1 is maintained (Doudna, J. A. et al., *Proc. Natl. Acad. Sci. USA* 86: 7402–7406 (1989)).

The sequence requirements for 3' splice-site selection appear to lie mainly within the structure of the intron itself, including helix P9.0 and the following guanosine residue which delineates the 3' intron boundary. However, flanking sequences within the 3' exon are required for the formation of helix P10 and efficient splicing, as shown by mutational analysis (Suh, E. R. et al., *Mol. Cell. Biol.* 10:2960–2965 (1990)). In addition, oligonucleotides have been ligated in trans, using a truncated form of the intron, and "external" guide sequence and oligonucleotides which had been extended by a 5' guanosine residue. The substrate oligonucleotides corresponding to 3' exon sequences were aligned solely by the formation of P10-like helices on an external template, prior to ligation (Doudna, J. A. et al., *Nature* 339:519–522 (1989)).

The cleavage activity of ribozymes has been targeted to specific RNAs by engineering a discrete "hybridization" region into the ribozyme, such hybridization region being capable of specifically hybridizing with the desired RNA. For example, Gerlach, W. L. et al., EP 321,201, constructed a ribozyme containing a sequence complementary to a target RNA. Increasing the length of this complementary sequence increased the affinity of this sequence for the target. However, the hybridizing and cleavage regions of this ribozyme were integral parts of each other. Upon hybridizing to the target RNA through the complementary regions, the catalytic region of the ribozyme cleaved the target. It was suggested that the ribozyme would be useful for the inactivation or cleavage of target RNA in vivo, such as for the treatment of human diseases characterized by the production of a foreign host'RNA. However, ribozyme-directed trans-splicing, (as opposed to trans-cleavage) was not described or suggested.

The endoribonuclease activities (the cleavage activities) of various naturally-occurring ribozymes have been extensively studied. Analysis of the structure and sequence of these ribozymes has indicated that certain nucleotides around the cleavage site are highly conserved but flanking sequences are not so conserved. This information has lead to the design of novel endoribonuclease activities not found in nature. For example, Cech and others have constructed novel ribozymes with altered substrate sequence specificity (Cech, T. R. et al., WO 88/04300; Koizumi, M. et al., *FEBS Lett.* 228:228–230 (1988); Koizumi, M. et al., *FEBS Lett.* 239:285–288 (1988); Haseloff, J. et al., *Nature* 334:585–591 (1987); and Heus, H. A. et al., *Nucl. Acids Res.* 18:1103–1108 (1990)). From early studies of the self-cleaving plant viroids and satellite RNAs (Buzayan, J. M. et al., *Proc. Natl. Acad. Sci. USA* 83:8859–8862 (1986), guidelines for the design of ribozymes that are capable of cleaving other RNA molecules in trans in a highly sequence specific have been developed (Haseloff, J. et al., *Nature* 334:585–591 (1988)). However, these constructs were unable to catalyze efficient, targeted trans-splicing reactions.

The joining of exons contained on separate RNAS, that is, trans-splicing, occurs in nature for both snRNP-mediated and self-catalyzed group I and group II introns. In trypanosome and *Caenorhabditis eleqans* mRNAs, common 5' leader sequences are transcribed from separate genes and spliced to the 3' portions of the mRNAs (Agabian, N., *Cell* 61:1157–1160 (1990); Hirsh, D. et al., *Mol. Biol. Rep.* 14:115 (1990). These small "spliced leader" RNAs (slRNAs) consist of the 5' exon fused to sequences that can functionally substitute for U1 snRNA in mammalian snRNP-splicing extracts.

Also, both the group I and group II self-splicing introns are capable of exon ligation in trans in artificial systems (Been, M. D. et al., *Cell* 47:207–216 (1986); Galloway-Salvo, J. L. et al., *J. Mol. Biol.* 211:537–549 (1990); Jacquier, A. et al., *Science* 234:1099–1194 (1986); and Jarrell, K. A. et al., *Mol. Cell Biol.* 8:2361–2366 (1988)). Trans-splicing occurs in vivo for group II introns in split genes of chloroplasts (Kohchi, T. et al., *Nucl. Acids Res.* 16:10025–10036 (1988)), and has been shown for a group I intron in an artificially split gene in *Escherichia coli* (Galloway-Salvo, J. L. et al., *J. Mol. Biol.* 211:537–549 (1990)). In the latter case, a bacteriophage T4 thymidylate synthase gene (td) containing a group I intron was divided at the loop connecting the intron helix P6a. Transcripts of the td gene segments were shown to undergo trzans-splicing in vitro, and to rescue dysfunctional *E. coli* host cells. Known base-pairings (P3, P6 and P6a) and possible tertiary interactions between the intron segments, allowed correct assembly and processing of the gene halves.

In vitro, the Tetrahymena ribozyme is capable of catalyzing the trans-splicing of single-stranded model oligoribonucleotide substrates. Four components were necessary: ribozyme, 3' single-stranded RNA, 5' exon and GTP. A shortened form of the Tetrahymena ribozyme (L-21 ScaI IVS RNA), starting at the internal guide sequence and terminating at $U_{409}$ has been used in such a reaction (Flanegan, J. B. et al., *J. Cell. Biochem.* (Supp.)12 part D: 28 (1988)). Attack by GTP at the 5' splice site released the 5' exon which was then ligated by the ribozyme to the 3' exon in a transesterification reaction at the 3' splice site.

The in vivo use of ribozymes as an alternative to the use of antisense RNA for the targeting and destruction of specific RNAs has been proposed (Gerlach, W. L. et al., EP321,201; Cotten, M., *Trends Biotechnol.* 8:174–178 (1990); Cotten, M. et al., *EMBO J.* 8:3861–3866 (1989); Sarver, N. et al., *Science* 247:1222–1225 (1990)). For example, expression of a ribozyme with catalytic endonucleolytic activity towards an RNA expressed during HIV-1 infection has been suggested as a potential therapy against human immunodeficiency virus type 1 (HIV-1) infection (Sarver, N. et al., *Science* 247:1222–1225 (1990); Cooper, M., *CDC AIDS Weekly*, Apr. 3, 1989, page 2; Rossi, J. J., Abstract of Grant No. 1RO1AI29329 in Dialog'Federal Research in Progress File 265). However, such attempts have not yet been successful.

In a study designed to investigate the potential use of ribozymes as therapeutic agents in the treatment of human immunodeficiency virus type 1 (HIV-1) infection, ribozymes of the hammerhead motif (Hutchins, C. J. et al., *Nucl. Acids Res.* 14:3627 (1986); Keese, P. et al., in *Viroids and Viroid-Like Pathogens*, J. S. Semancik, ed., CRC Press, Boca Raton, Fla., 1987, pp. 1–47) were targeted to the HIV-1 gag transcripts. Expression of the gag-targeted ribozyme in human cell cultures resulted in a decrease (but not a complete disappearance of) the level of HIV-1 gag RNA and in antigen p24 levels (Sarver, N. et al., *Science* 247:1222–1225 (1990)). Thus, the medical effectiveness of Sarver'ribozyme was limited by its low efficiency since any of the pathogen'RNA that escapes remains a problem for the host.

Another problem with in vivo ribozyme applications is that a high ribozyme to substrate ratio is required for ribozyme inhibitory function in nuclear extracts and it has been difficult to achieve such ratios. Cotton et al. achieved a high ribozyme to substrate ration by microinjection of an expression cassette containing a ribozyme-producing gene operably linked to a strong tRNA promoter (a polymerase III promoter) in frog oocytes, together with substrate RNA that contains the cleavage sequence for the ribozyme (Cotton, M. et al., *EMBO J.* 8:3861–3866 (1989). However, microinjection is not an appropriate method of delivery in multicellular organisms.

The in vivo activity of ribozymes designed against mRNA coding for *Escherichia coli* β-galactosidase has been reported (Chuat, J.-C. et al., *Biochem. Biophys. Res. Commun.* 162:1025–1029 (1989)). However, this activity was only observed when the ribozyme and target were transfected into bacterial cells on the same molecule. Ribozyme activity was inefficient when targeted against an mRNA transcribed from a bacterial F episome that possessed the target part of the β-galactosidase gene.

Thus, current technological applications of ribozyme activities are limited to those which propose to utilize a ribozyme'cleavage activity to destroy the activity of a target RNA. Unfortunately, such applications often require complete destruction of all target RNA molecules, and/or relatively high ribozyme:substrate ratios to ensure effectiveness and this has been difficult to achieve. Most importantly, the modified ribozymes of the art are not capable of efficient, directed trans-splicing.

Accordingly, a need exists for the development of highly efficient ribozymes and ribozyme expression systems. Especially, the art does not describe an effective means in which to destroy an existing RNA sequence or to alter the coding sequence of an existing RNA by the trans-splicing of a new RNA sequence into a host'RNA.

SUMMARY OF THE INVENTION

Recognizing the potential for the design of novel ribozymes, and cognizant of the need for highly efficient methods to alter the genetic characteristics of higher eukaryotes in vivo, the inventors have investigated the use of ribozymes to alter the genetic information of native RNA'in vivo. These efforts have culminated in the development of highly effective trans-splicing ribozymes, and guidelines for the engineering thereof.

According to the invention, there is first provided an RNA or DNA molecule, such molecule encoding a trans-splicing ribozyme, such ribozyme being capable of efficiently splicing a new 3' exon sequence into any chosen target RNA sequence in a highly precise manner, in vitro or in viva, and such molecule being novel in the ability to accommodate any chosen target RNA or 3' exon sequences, and in the addition of a complementary sequence which enhances the specificity of such ribozyme.

According to the invention, there is also provided an RNA or DNA molecule, such molecule encoding a ribozyme, the sequence for such ribozyme being a fusion RNA, such fusion RNA providing a first RNA sequence that is sufficient for targeting such ribozyme to hybridize to a target RNA, and further a second RNA sequence, such second RNA sequence capable of being transposed into the target RNA, and such second RNA sequence encoding an RNA sequence foreign to the targeted RNA sequence.

According to the invention, there is also provided an RNA or DNA molecule, such molecule encoding a conformationally disrupted ribozyme of the invention, a pro-ribozyme, such pro-ribozyme being substrate-activated, that is, such pro-ribozyme possessing neglible or no self-cleavage or trans-splicing activity, until being reactivated by specific interaction with target RNA.

According to the invention, there is further provided an RNA or DNA molecule containing a ribozyme or pro-ribozyme expression cassette, such cassette being capable of being stably maintained in a host, or inserted into the genome of a host, and such cassette providing the sequence of a promoter capable of functioning in such host, operably linked to the sequence of a ribozyme or pro-ribozyme of the invention.

According to the invention, there is further provided a method for in-vitro trans-splicing, such method comprising the steps of (1) providing a ribozyme or pro-ribozyme of the invention and an appropriate substrate for such ribozyme or pro-ribozyme in vitro, (2) further providing in vitro reaction conditions that promote the desired catalytic activity of such ribozyme or pro-ribozyme; and (3) allowing such ribozyme or pro-ribozyme to react with such substrate under such conditions.

According to the invention, there is further provided a method for in vivo trans-splicing, such method comprising the steps of (1) providing an RNA or DNA molecule of the invention to a host cell, (2) expressing the ribozyme or pro-ribozyme encoded by such molecule in such host cell, (3) expressing a substrate of such ribozyme or pro-ribozyme in such host cell, and (4) allowing such ribozyme or pro-ribozyme to react with such substrate in such host cell.

According to the invention, there is further provided a method for inactivating the activity of a target RNA, such method comprising (1) providing a ribozyme or pro-ribozyme of the invention, such ribozyme or pro-ribozyme being catalytically active against such target RNA, (2) providing such target RNA, and (3) providing conditions that allow such ribozyme or pro-ribozyme to express its catalytic activity towards such target RNA.

According to the invention, there is further provided a method for providing a desired genetic sequence to a host cell in vivo, such method comprising (1) providing a ribozyme or pro-ribozyme of the invention to a desired host cell, such ribozyme or pro-ribozyme being catalytically active against a target RNA in such host cell, (2) providing such ribozyme or pro-ribozyme encoding such desired genetic sequence, and (3) providing conditions that allow such ribozyme or pro-ribozyme to trans-splice such desired genetic sequence into the sequence of the target RNA.

According to the invention, there is further provided a method for engineering male or female sterility in agronomically important plant species, such method comprising providing a ribozyme or pro-ribozyme of the invention to a desired cell of such species, such ribozyme or pro-ribozyme being targeted to any RNA expressed in a cell necessary for fertility, such ribozyme or pro-ribozyme providing a sequence encoding a toxic product to the trans-spliced RNA.

According to the invention, there is further provided a method of modifying the genetics of crop plants, such method comprising providing a germ cell of such crop plant with a ribozyme of the invention, such ribozyme encoding a sequence capable of conferring such desired genetic modification in such plant.

According to the invention, there is further provided a method of immunizing plants against plant pathogens, such method comprising the construction of transgenic plants capable of expressing a plant pathogen-specific fusion ribozyme of the invention, and such ribozyme being capable of destroying or inhibiting the pathogen.

According to the invention, there is further provided a transformed, pathogen-resistant microorganism, such microorganism being resistant to a desired pathogen, such microorganism being transformed with a ribozyme of the invention and such ribozyme providing a catalytic activity that targets a nucleic acid molecule expressed by such pathogen.

According to the invention, there is further provided a viral pathogen capable of delivering a desired ribozyme activity to a desired host, such ribozyme activity being delivered by a ribozyme of the invention.

DESCRIPTION OF THE FIGURES

FIG. 1 is a diagram of the mechanism of ribozyme splicing of the group I intron.

FIG. 3A is a diagram of the design of a CAT-LacZ α-peptide trans-splicing ribozyme; 3B is the complete DNA sequence of the CAT-LacZ ribozyme.

FIGS. 4A–4C present the sequences of cucumber mosaic virus (CMV) RNA 4 trans-splicing ribozymes. FIG. 4A virus RNA target sequences; FIG. 4B: Oligonucleotide target sequences; FIG. 4C: CMV RNA4—diphtheria toxin A-chain trans-splicing ribozymes.

FIG. 5 is a comparison of cucumber mosaic virus 3/4 sequences.

FIG. 6A presents a partial sequence of wild-type DTA and DTA 3' and exon mutants. FIG. 6C is the complete coding sequence of a Gal4-DTA ribozyme with the isoleucine substitution.

FIGS. 7A–7D present the rationale for "pro-ribozyme" design. Arrows show sites of ribozyme cleavage, "antisense" regions are shown in black, catalytic domains are shown with radial shading, and 3' "exon" sequences are shown with light shading. In the absence of the target mRNA, trans-splicing ribozymes may transiently base-pair, and react with heterologous sequences (including their own). In addition, scission at the "3' exon" junction will occur. Inactive "pro-ribozymes" are constructed to contain extra self-complementary sequences which cause the catalytic center of the ribozyme to be mis-folded. Active ribozymes are only formed after base-pairing with the intended target mRNA— and consequent displacement of the interfering secondary structure.

FIG. 8C shows P8 helices for the unmodified ribozyme and pro-ribozymes 1 and 2, with 13 and 18 nucleotides, respectively, of sequence complementary to the "antisense" region (highlighted).

FIG. 9B shows the active pro-ribozyme, after base-pairing with the CAT mRNA, displacement of the helix P8—"antisense" pairing, and re-formation of helix P8.

FIG. 12 shows the "wild-type" and modified helices P8 used for pro-ribozyme design with possible base-pairs indicated in schematic form. Those bases which are complementary to the "anti-sense" portion of the corresponding pro-ribozyme, are shown in bold type. The number of complementary bases is listed next to each helix. The helices are ordered by the stability of the corresponding pro-ribozyme transcripts, as measured by the degree of "3' exon" hydrolysis during in vitro transcription.

DETAILED DESCRIPTION OF THE PREFERRED EMBODIMENTS

I. Definitions

Figure 2A:
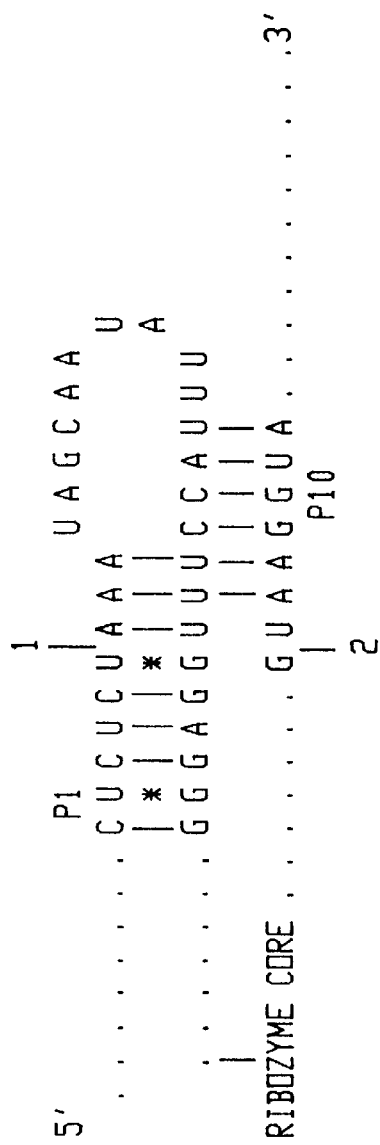
FIG. 2A is a diagram of structure of the *Tetrahymena thermophila* rRNA intron.

In the description that follows, a number of terms used in recombinant DNA (rDNA) technology are extensively utilized. In order to provide a clear and consistent understanding of the specification and claims, including the scope to be given such terms, the following definitions are provided.

Ribozyme. An RNA molecule that inherently possesses catalytic activity.

Trans-splice. A form of genetic manipulation whereby a nucleic acid sequence of a first polynucleotide is colinearly linked to or inserted colinearly into the sequence of a second polynucleotide, in a manner that retains the 3'→5' phosphodiester linkage between such polynucleotides. By "directed" trans-splicing or "substrate-specific" trans-splicing is meant a trans-splicing reaction that requires a specific specie of RNA as a substrate for the trans-splicing reaction (that is, a specific specie of RNA in which to splice the transposed sequence). Directed trans-splicing may target more than one RNA specie if the ribozyme is designed to be directed against a target sequence present in a related set of RNAs.

Target RNA. An RNA molecule that is a substrate for the catalytic activity of a ribozyme of the invention.

Expression Cassette. A genetic sequence that provides sequences necessary for the expression of a ribozyme of the invention.

Stably. By "stably" inserting a sequence into a genome is intended insertion in a manner that results in inheritance of such sequence in copies of such genome.

Operable linkage. An "operable linkage" is a linkage in which a sequence is connected to another sequence (or sequences) in such a way as to be capable of altering the functioning of the sequence (or sequences). For example, by operably linking a ribozyme encoding sequence to a promoter, expression of the ribozyme encoding sequence is placed under the influence or control of that promoter. Two nucleic acid sequences (such as a ribozyme encoding sequence and a promoter region sequence at the 5' end of the encoding sequence) are said to be operably linked if induction of promoter function results in the transcription of the ribozyme encoding sequence and if the nature of the linkage between the two sequences does not (1) result in the introduction of a frame-shift mutation, (2) interfere with the ability of the expression regulatory sequences to direct the expression of the ribozyme. Thus, a promoter region would be operably linked to a nucleic acid sequence if the promoter were capable of effecting the synthesis of that nucleic acid sequence.

II. Engineering of the Ribozyme of the Invention The trans-splicing ribozymes, pro-ribozymes and methods of the invention provide, for the first time, a ribozyme capable of directed trans-splicing into any RNA sequence, and especially into mature (non-intron-containing) mRNA. The trans-splicing ribozyme as described herein, with its extended complementarity to the target, greatly differs from *T. thermophila* derived endoribonuclease activities described in the art. The additional complementarity of the ribozymes of the invention confers increased affinity and specificity for the target and the complementarity is not an integral part of the catalytic activity. In addition, cleavage occurs efficiently and precisely in the absence of denaturants and at high concentrations of $Mg^{++}$.

The guidelines described herein for the design of trans-splicing ribozymes are conservative, based on the well characterized properties of group I self-splicing introns and are meant to provide a general scheme for the design of any directed trans-splicing ribozyme. Accordingly, the guidelines presented herein are not limited to the group I intron of the *T. thermophila* pre-mRNA and may be used by one of skill in the art to design a ribozyme of the invention with other group I introns using such guidelines and knowledge in the art. The native *T. thermophila* ribozyme (the intron sequence) is located from base 53 to base 465 in the sequence below of the *T. thermophila* extrachromosomal rDNA:

```
TGACGCAATT CAACCAAGCG CGGGTAAACG GCGGGAGTAA CTATGACTCT [SEQ ID NO.1]

CTAAATAGCA ATATTTACCT TTGGAGGGAA AAGTTATCAG GCATGCACCT

CCTAGCTAGT CTTTAAACCA ATAGATTGCA TCGGTTTAAA AGGCAAGACC

GTCAAATTGC GGGAAAGGGG TCAACAGCCG TTCAGTACCA AGTCTCAGGG

GAAACTTTGA CATGGCCTTG CAAAGGGTAT GGTAATAAGC TGACGGACAT

GGTCCTAACC ACGCAGCCAA GTCCTAAGTC AACAGATCTT CTGTTGATAT

GGATGCAGTT CACAGACTAA ATGTCGGTCG GGGAAGATGT ATTCTTCTCA

TAAGATATAG TCGGACCTCT CCTTAATGGG AGGTAGCGGA TGAATGGATG

CAACACTGGA GCCGCTGGGA ACTAATTTGT ATGCGAAAGT ATATTGATTA

GTTTTGGAGT ACTCGTAAGG TAGCCAAATG CCTCGTCATC TAATTAGTGA

CGCGCATGAA TGGATTA
```

(Kan, N. C. et al., *Nucl. Acids Res.* 10:2809–2822 (1982)).

As described herein, the directed trans-splicing ribozymes of the invention are engineered using the catalytic core of this intron. The intron, and its catalytic core can be isolated by methods known in the art. The catalytic core of the intron, that is, the truncated intron, differs form the full-length intron only in that it is truncated at the ScaI site, thus removing the last five nucleotides of the intron. The truncated intron RNA may be prepared by techniques known in the art or may be purchased commercially in kit form from commercial sources such as, for example, product #72000 from US Biochemical, Cleveland, Ohio (RNAzyme™ Tet 1.0 Kit). This US Biochemical kit provides ribozyme and the protocol for the use of the ribozyme. Transcribed Tet.1 cDNA may be used as the substrate for polymerase chain reaction (PCR) mutagenesis as described below, to produce a synthetic trans-splicing enzyme.

Substrate specificity of the ribozyme of the invention, that is, the ability of the ribozyme to "target" a specific RNA as a substrate, is conferred by fusing complementary sequences specific to the target (substrate) RNA to the 5' terminus of the ribozyme.

Directed trans-splicing specificity of the ribozyme of the invention, that is, specificity in trans-splicing a desired foreign sequence of interest with the sequence of a target RNA, is conferred by providing a new 3' exon at the 3' terminus of the ribozyme. Details of the design are further provided below.

To alter the structural and catalytic properties of the Group I introns, exon sequences replace the flanking sequences of such introns so that only the catalytic core of the intron, the ribozyme, remains. The resulting modified ribozyme can interact with substrate RNAs in trans. When truncated forms of the intron (i.e., the catalytic "core," i.e. truncated at the ScaI site, removing the last five nucleotides of the intron) are incubated with sequences corresponding to the 5' splice junction of the native ribozyme, the site undergoes guanosine-dependent cleavage in mimicry of the first step in splicing.

Engineering of the ribozymes of the invention requires consideration of the four guidelines that follow.

First, a splice site must be chosen within the target RNA. In the final trans-splicing complex, only the 5' portion of the P1 duplex is contributed by the target RNA. Only a single conserved residue, uracil, is required immediately 5' of the intended splice site. This is the sole sequence requirement in the target RNA. There is no inate structure required of the target RNA. Mature mRNA may be targeted and the trans-splicing reaction performed in the cell's cytoplasm rather than in the nucleus (against pre-mRNA). This obviates the need for high concentrations of ribozyme in a cell's nucleus.

Second, having chosen a particular target sequence, compensating sequence changes must be added to the 5' section of the ribozyme in order to allow the formation of a suitable helix P1 between the target and ribozyme RNAS. It is highly desired is that the helix P1 should contain a U:G base-pair at the intended 5' splice site, and should be positioned at the 4th, 5th (preferred) or 6th position from the base of the helix (Doudna, J. A., et al., "RNA Structure, Not Sequence Determines The 5' Splice-Site Specificity of a Group I Intron," *Proc. Natl. Acad. Sci. USA* 86:7402–7406 (1989), incorporated herein by reference). For the native *T. thermophila* intron, P1 extends for an additional 3 base pairs past the intended 5' splice site, and, in a preferred embodiment, this is maintained in the trans-splicing ribozyme of the invention. For trans-splicing to be efficient, the substrate and endoribonucleolytic intron RNAs must base-pair to form helix P1, with a resulting wobble U:G base-pair. Cleavage of the target RNA occurs at the phosphodiester bond immediately 3' to (after the) U:G base-pair. Phylogenetic comparisons and mutational analyses indicate that the nature of the sequences immediately adjacent the conserved uracil residue at the 5' splice site are unimportant for catalysis, provided the base-pairing of helix P1 is maintained.

Figure 2B:
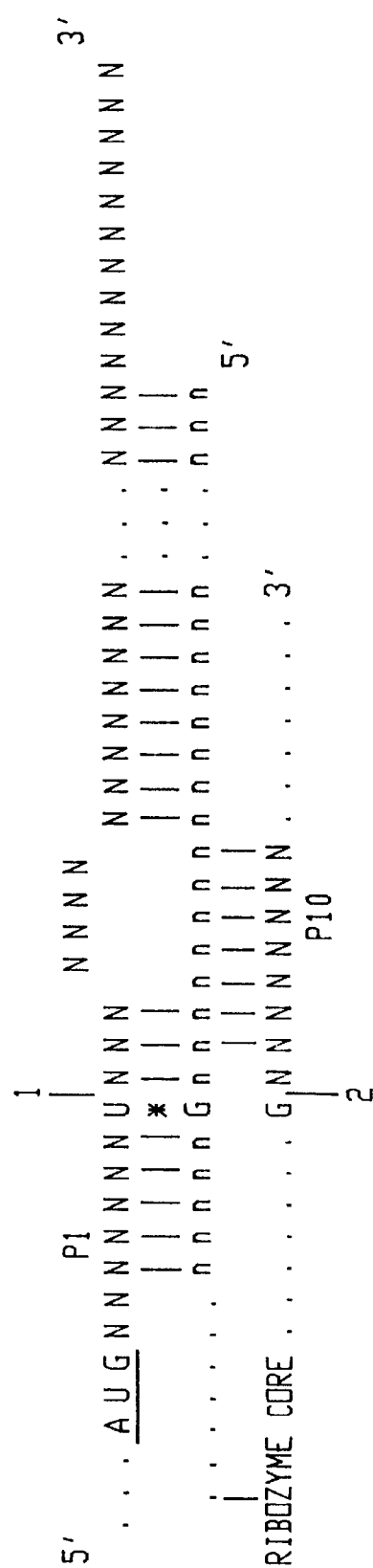
FIG. 2B Target mRNA and trans-splicing ribozyme of the invention.

Third, the exon sequences flanking the 3' splice site must be chosen, and adjustments made in the 5' section of the ribozyme, if necessary, to allow the formation of a stable P10 helix. While the P10 helix may be dispensesd with if necessary, its presence enhances splicing and preferred embodiments of the ribozyme of the invention retain the P10 helix (Suh, E. R. et al., "Base Pairing Between The 3' Exon And An Internal Guide Sequence Increases 3' Splice Site Specificity in the Tetrahymena Self-Splicing rRNA Intron," *Mol. Cell. Biol.* 10:2960–2965 (1990)). The helices P1 and P10 overlap along the *T. thermophila* intron IGS, and the 2nd and 3rd residues following both the 5' and 3' splice sites are complementary to the same residues in the IGS FIGS. 2A and 2B. While there may be some advantage in following this, many natural group I introns do not share this constraint, so the choice of 3' exon sequences may be determined primarily by experimental considerations. Such considerations reflect the wide flexibility in choice of splice sites. For example, if it is desired to join two sequences at a given point, the sequence at such point cannot be mutated or otherwise altered by the trans-splicing event. Either P1 or P10 can be made shorter if the overlapping sequences don't otherwise accomodate the desired splice site.

The sequence requirements for 3' splice-site selection appear to lie mainly within the structure of the intron (the ribozyme) itself, including helix P9.0 and the adjoining 3' guanosine residue which delineates the 3' intron boundary. P9.0 is wholly contained within the intron sequences and helps define the adjacent 3' splice site. For the trans-splicing (3) the chosen "3' exon" sequences are fused to the 3' portion of the ribozyme, maintaining the conserved helix P10; and (4) to increase affinity for the target RNA, if desired, a section of extended sequence complementarity is fused to the 5' portion of the ribozyme to allow the formation of 30–40 base-pairs.

The alignment of the resulting trans-splicing ribozyme with its target RNA may be diagrammed as shown immediately below. The target RNA sequence represents the top line. The ribozyme sequence is aligned below it, a continuous sequence wrapping around the lower two lines wherein the hybridization of the nucleotides at the 5' and 3' ends, and P1 and P10, of the ribozyme may be seen.

Alignment of the Ribozyme of the Invention with a Target RNA

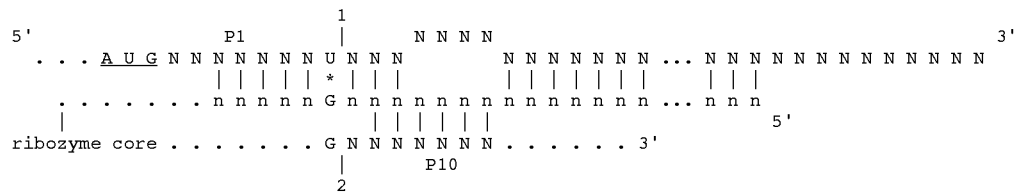

design, the P9.0 helix and the rest of the functional RNA elements within the intron are not altered. The structural characteristics of the P9.0 helix are known (Michel, F. et al., "The Guanosine Binding Site of the Tetrahymena Ribozyme," Nature 342:391–395 (1989)). However, flanking sequences within the 3' exon are required for the formation of helix P10 and efficient splicing, as shown by mutational analysis.

Fourth, a region of complementary sequence is placed at the 5' terminus of the trans-splicing ribozyme in order to increase its affinity and specificity for the target RNA. The sequences involved in complementarity do not immediately abut sequences involved in P1 helix formation but are separated by, for example, five nucleotides also involved in P10 formation. As shown herein, an arbitrary length of around 40 residues has been used. Other lengths may be used provided they are not detrimental to the desired effect.

For example, starting with the T. thermophila self-splicing intron (diagrammed below):

According to the invention, trans-splicing ribozymes can be designed that will trans-splice essentially any RNA sequence onto any RNA target. It is not necessary that the target contain an intron sequence or that the ribozyme be an intron in the target sequence. For example, a strategy for such design may include (1) the identification of the desired target RNA (2) cloning and/or sequencing of the desired target RNA or portion thereof (3) selection of a desired coding sequence to trans-splice into the target RNA, (4) the construction of a ribozyme of the invention capable of hybridizing to such target using the guidelines herein and (5) confirmation that the ribozyme of the invention will utilize the target as a substrate for the specific trans-splicing reaction that is desired and (6) the insertion of the ribozyme into the desired host cell.

Choice of a target RNA will reflect the desired purpose of the trans-splicing reaction. If the purpose of the reaction is to inactivate a specific RNA, then such RNA must be trans-spliced at a position that destroys all functional peptide domains encoded by such RNA and at a position that does

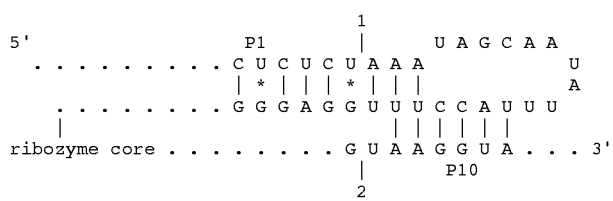

(The "1" and "2" in the above diagram (and in other ribozyme diagrams throughout the application) note the first and second splice sites, respectively.)

(1) a "5" site is chosen adjacent to a uracil residue within a chosen target RNA;

(2) sequences complementary to the chosen RNA are fused to the 5' portion of the self-splicing Group I intron. Base-pairing between ribozyme and target RNA allow formation the of the helix P1;

not result in continued expression of the undesired genetic sequences. If more than one allele of the gene encoding such RNA exists, the ribozyme should preferably be designed to inactivate the target RNA at a site common to all expressed alleles. Alternatively, more than one ribozyme may be provided to the cell, each designed to inactivate a specific allelic form of the target RNA.

When only inactivation of the target RNA is desired, and not the expression of a new, desired RNA sequence, it is not necessary that the foreign RNA donated by the ribozyme provide a sequence capable of being translated by the host cell, and a sequence containing translational stop codons may be used as a truncated intron, for example, the intron ribozyme truncated at the ScaI site.

If the purpose of the trans-splicing reaction is to provide a genetic trait to a host cell, then the choice of target RNA will reflect the desired expression pattern of the genetic trait. If it is desired that the genetic trait be continuously expressed by the host, then the target RNA should also to be continuously expressed. If it is desired that the genetic trait be selectively expressed only under a desired growth, hormonal, or environmental condition, then the target RNA should also be selectively expressed under such conditions.

It is not necessary that expression of the ribozyme itself be selectively limited to a desired growth, hormonal, or environmental condition if the substrate for such ribozyme is not otherwise present in the host as the ribozyme itself is not translated by the host. Thus, sequences encoded by the RNA donated by the ribozyme of the invention are not translated until the trans-splicing event occurs and such event may be controlled by the expression of the ribozyme substrate in the host.

If desired, expression of the ribozyme may be engineered to occur in response to the same factors that induce expression of a regulated target, or, expression of the ribozyme may be engineered to provide an additional level of regulation so as to limit the occurrence of the trans-splicing event to those conditions under which both the ribozyme and target are selectively induced in the cell, but by different factors, the combination of those factors being the undesired event. Such regulation would allow the host cell to express the ribozyme's target under those conditions in which the ribozyme itself was not co-expressed.

The sequence of the ribozyme domain that hybridizes to the target RNA is determined by the sequence of the target RNA. The sequence of the target RNA is determined after cloning sequences encoding such RNA or after sequencing a peptide encoded by such target and deducing an RNA sequence that would encode such a peptide. Cloning techniques known in the art may be used for the cloning of a sequence encoding a target RNA.

The selection of a desired sequence to be trans-spliced into the target RNA (herein termed the "trans-spliced sequence") will reflect the purpose of the trans-splicing. If a trans-splicing event is desired that does not result in the expression of a new genetic sequence, then the trans-spliced sequence need not encode a translatable protein sequence. If a trans-splicing event is desired that does result in the expression of a new genetic sequence, and especially a new peptide or protein sequence, then the trans-spliced sequence may further provide translational stop codons, and other information necessary for the correct translational processing of the RNA in the host cell. If a specific protein product is desired as a result of the trans-splicing event, then it would be necessary to maintain the amino acid reading frame in the resulting fusion.

The identification and confirmation of the specificity of a ribozyme of the invention is made by testing a putative ribozyme's ability to catalyze the desired trans-splicing reaction in the presence of the desired target sequence. The trans-splicing reaction should not occur if the only RNA sequences present are non-target sequences to which such ribozyme should not be responsive (or less responsive). Such characterization may be performed with the assistance of a marker such that correct (or incorrect) ribozyme activity may be more easily monitored. In most cases, it is sufficient to test the ribozyme against its intended target in vitro and then transform a host cell with it for study of its in vivo effects.

When it is desired to eliminate a host's RNA, such elimination should be as complete as possible. When it is desired to provide a new genetic sequence to a host cell, the trans-splicing reaction of the invention need not be complete. It is an advantage of the invention that, depending upon the biological activity of the peptide that is translated from such genetic sequence, the trans-splicing event may in fact be quite inefficient, as long as sufficient trans-splicing occurs to provide sufficient mRNA and thus encoded polypeptide to the host for the desired purpose.

Transcription of the ribozyme of the invention in a host cell occurs after introduction of the ribozyme gene into the host cell. If the stable retention of the ribozyme by the host cell is not desired, such ribozyme may be chemically or enzymatically synthesized and provided to the host cell by mechanical methods, such as microinjection, liposome-mediated transfection, electroporation, or calcium phosphate precipitation. Alternatively, when stable retention of the gene encoding the ribozyme is desired, such retention may be achieved by stably inserting at least one DNA copy of the ribozyme into the host's chromosome, or by providing a DNA copy of the ribozyme on a plasmid that is stably retained by the host cell.

Preferably the ribozyme of the invention is inserted into the host's chromosome as part of an expression cassette, such cassette providing transcriptional regulatory elements that will control the transcription of the ribozyme in the host cell. Such elements may include, but not necessarily be limited to, a promoter element, an enhancer or UAS element, and a transcriptional terminator signal. Polyadenylation is not necessary as the ribozyme is not translated. However, such polyadenylation signals may be provided in connection with the sequence encoding the element to be trans-spliced.

Expression of a ribozyme whose coding sequence has been stably inserted into a host's chromosome is controlled by the promoter sequence that is operably linked to the ribozyme coding sequences. The promoter that directs expression of the ribozyme may be any promoter functional in the host cell, prokaryotic promoters being desired in prokaryotic cells and eukaryotic promoters in eukaryotic cells. A promoter is composed of discrete modules that direct the transcriptional activation and/or repression of the promoter in the host cell. Such modules may be mixed and matched in the ribozyme's promoter so as to provide for the proper expression of the ribozyme in the host. A eukaryotic promoter may be any promoter functional in eukaryotic cells, and especially may be any of an RNA polymerase I, II or III specificity. If it is desired to express the ribozyme in a wide variety of eukaryotic host cells, a promoter functional in most eukaryotic host cells should be selected, such as a rRNA or a tRNA promoter, or the promoter for a widely expressed mRNA such as the promoter for an actin gene, or a glycolytic gene. If it is desired to express the ribozyme only in a certain cell or tissue type, a cell-specific (or tissue-specific) promoter elements functional only in that cell or tissue type should be selected.

The trans-splicing reaction is chemically the same whether it is performed in vitro or in vivo. However, in vivo, since cofactors are usually already present in the host cell, the presence of the target and the ribozyme will suffice to result in trans-splicing.

The embodiments described above would also apply to the construction of pro-ribozymes. A trans-splicing ribozyme, as described above, consists of three fused sequence elements—a 5' "anti-sense" region which is complementary to the target RNA, the catalytic region which is based on a self-splicing Group I intron, and 3' "exon" sequences. The 5' region can base pair with the chosen target RNA, to bring it into proximity with the catalytic sequences of the Group I intron. The structure of the Group I intron provides a chemical environment suitable to catalyze the precise splicing of the target RNA with the 3' "exon" sequences. However, in the absence of the appropriate target RNA, the ribozyme sequences can still catalyze scission at the 3' "exon" junction (similar hydrolysis is seen for Group I self-splicing intons (Zaug et al., *Science* 231:470–475 (1986)), and may be able to catalyze illegitimate splicing events through transient base-pairing of the ribozyme with heterologous RNA sequences (which may include their own). Such side-reactions and illegitimate splicing events are unwanted, and may be deleterious. For example, if trans-splicing is to be used for conditional delivery of a toxin in vivo, illegitimate trans-splicing might result in unexpected expression of the toxic activity. Spontaneous cleavage at the 3' "exon" junction would lower the efficiency of trans-splicing.

To help avoid these problems, "pro-ribozyme" forms of the trans-splicing RNAs have been constructed wherein a conserved helix (for example, helix P8) is disrupted. The pro-ribozymes are constructed to contain extra self-complementary sequences which cause the catalytic center of the ribozyme to be mis-folded. The pro-ribozymes are inactive in the absence of the intended target RNA; active forms are only formed after base-pairing of the ribozyme and target RNAs—with consequent displacement of the interfering secondary structure within the ribozyme. Pro-ribozymes are intended to be catalytically inert species in the absence of the target RNA, to eliminate unwanted self-cleavage, self-splicing and illegitimate trans-splicing reactions in vitro and in vivo (FIGS. 7A–7D)

The pro-ribozymes described here are conformationally disrupted and therefore inactive forms of the trans-splicing activities. Thus the pro-ribozymes possess little self-cleavage activity. They are only re-activated by specific interaction with the target RNA, and thus are substrate-activated ribozymes which are less likely to catalyze trans-splicing to an unintended target RNA. Trans-splicing ribozymes are intended to be used for the delivery of new gene activities in vivo, and any reduction in the extent of unwanted side reactions or illegitimate splicing is desirable, and may be necessary.

While the disruption of helix P8 has been exemplified here for the trans-splicing pro-ribozymes, other helices which are required for catalytic activity could also have been used.

The same approach, of disrupting the conformation of a catalytically important structure in such a way that only base-pairing with the intended substrate RNA will allow the formation of an active ribozyme, could be applied to other ribozyme designs. For example, the loop sequence of a "hammerhead" type endoribonuclease (Haseloff et al., *Nature* 334:585–591 (1988)) could be extended and made complementary to one of the "anti-sense" arms of the ribozyme—similar to the above modification of helix P8. Endoribonuclease activity would only be exhibited after base-pairing with the chosen target RNA, displacement of the disrupting secondary structure, and reformation of the stem-loop structure required for catalysis. This would effectively increase the specificity of the ribozyme of its target.

In addition, the activation of a pro-ribozyme need not rely on base-pairing with the substrate itself. Instead, a chosen third RNA or ssDNA or even protein might be required for activity. An additional base-pairing or RNA-protein interaction would be required for the formation of an active ribozyme complex. The availability of such additional components would determine ribozyme activity, and could be used to alter ribozyme selectivity.

The trans-splicing ribozymes, pro-ribozymes, and methods of the invention are useful in producing a gene activity useful for the genetic modification of targeted cells. For example, the trans-splicing reaction of the invention is useful to introduce a protein with toxic properties into a desired cell. The susceptibility of cells will be determined by the choice of the target RNA and the regulatory controls that dictate expression of the ribozyme. For example, a ribozyme or pro-ribozyme that transposes an RNA sequence encoding a toxic protein may be engineered so that expression of the ribozyme or pro-ribozyme will depend upon the characteristics of an operably-linked promoter. In a highly preferred embodiment, diphtheria toxin peptide A is encoded by that part of the ribozyme that is trans-spliced into a desired target in the host. Conditional expression of the ribozyme and diphtheria toxin peptide A chain results in the death of the host cell. Other potentially useful peptide toxins include ricin, exotoxin A, and herpes thymidine kinase (Evans, G. A., *Genes & Dev.* 3:259–263 (1989)). In addition, various lytic enzymes have the potential for disrupting cellular metabolism. For example, a fungal ribonuclease may be used to cause male sterility in plants (Mariani, C. et al., *Nature* 347:737–741 (1990)). Particular tissues might be destroyed due to limited expression of the target RNA. Further, if a viral RNA is used as target, new forms of virus resistance, or therapies may be engineered.

The ribozyme or pro-ribozyme of the invention may be introduced into any host cell, prokaryotic or eukaryotic and especially into a plant or mammalian host cell, and especially a human cell, either in culture or in vivo, using techniques known in the art appropriate to such hosts. The ribozymes or pro-ribozyme of the invention may also be engineered to destroy viruses. In one embodiment, the ribozyme or pro-ribozyme of the invention is provided in a genetically stable manner to a host cell prior to a viral attack. Infection by the appropriate virus, or expression of the latent virus in such host cell, (resulting in the appearance of the ribozyme's or pro-ribozyme target RNA in the host cell), would stimulate the catalytic activity of the ribozyme and destruction of the viral RNA target and/or production of a toxin via trans-splicing resulting in death of the virus-infected cell. In another embodiment, the ribozyme or pro-ribozyme may be engineered and packaged into the virus itself. Such embodiments would be especially useful in the design of viruses for investigative purposes, wherein the ribozyme or pro-ribozyme may be designed to destroy the function of a specific viral RNA and thus allow the study of viral function in the absence of such RNA. Viruses carrying ribozymes or pro-ribozyme may also be used as carriers to transfect host cells with a desired ribozyme or pro-ribozyme activity.

Male or female sterility may be engineered in agronomically important species using the ribozymes or pro-ribozymes of the invention. For example, male sterility in tobacco may be engineered by targetting TA29 or TA13 mRNA (tobacco anther-specific genes; Seurinck, J. et al., *Nucl. Acids Res.* 18:3403 (1990) with a ribozyme or pro-ribozyme of the invention that trans-splices the DTA 3' exon into those targets.

The form of crop plants may be manipulated by selective destruction or modification of tissues using the ribozymes or pro-ribozymes of the invention. For example, seedless fruits may be made by targetting the seed storage protein mRNA with a ribozyme or pro-ribozyme of the invention that trans-splices the DTA 3' exon into the target.

Transgenic plants may be protected against infection by expression of virus-specific ribozymes or pro-ribozymes to kill infected cells. This would be an artificial form the "hypersensitive response." For example, cucumber mosaic virus coat protein mRNA may be targeted with a ribozyme or pro-ribozyme of the invention that trans-splices the DTA 3' exon into the target.

Populations of micro-organisms may be made resistant to specific pathogens by introduction of trans-splicing ribozymes or pro-ribozymes. For example, cheese-making bacteria may be made resistant to phage infection by targetting the phage RNA with a bacterial toxin gene or lytic enzyme encoded by the 3' exon provided by the ribozyme or pro-ribozyme of the invention, for example, which would interfere with phage replication by causing premature lysis after phage infection.

Virus pathogens could be constructed to deliver toxic activities via trans-splicing. In this way, specific cell types could be targeted for ablation, such as for cancer or viral therapy. For example, HIV mRNA may be targeted by a ribozyme or pro-ribozyme of the invention that carries the DTA 3' exon, for either virus or liposome delivery.

The examples below are for illustrative purposes only and are not deemed to limit the scope of the invention.

EXAMPLES

Example 1

Construction and Characterization of a CAT-LacZ Trans-Splicing Ribozyme

I. PCR Amplification and Cloning of the Ribozyme of the Invention

Following the guidelines outlined above, a trans-splicing fusion ribozyme was designed that will splice a portion of the amino-terminal coding sequence of *E. coli* β-galactosidase (LacZ) mRNA to a site in the chloramphenicol acetyl transferase (CAT) mRNA (FIGS. 3A and 3B). The sections of new sequence flanking the *T. thermophila* ribozyme core and the 3' exon were synthesized as oligonucleotides. The intact ribozyme sequence was then assembled by successive polymerase chain reactions, using the synthetic adaptor oligonucleotides as primers with ribozyme and β-galactosidase DNA templates (while there are other methods available, this method is most convenient).

For the construction of a ribozyme capable of splicing β-galactosidase (LacZ) α-peptide coding sequence to a site in the 5' coding sequence of the chloramphenicol acetyl transferase (CAT), three oligonucleotides were synthesized.

Oligonucleotide 1
5'-GGCCA AGCTT CTTTA CGATG CCATT GGGAT ATATC AACGG TGGTA TAAAC CCGTG GTTTT TAAAA GTTAT CAGGC ATGCA CC-3' [SEQ ID NO. 2]

Oligonucleotide 2
5'-GATTA GTTTT GGAGT ACTCG TACGG ATTCA CGGCC GTCGT TTTAC AA-3' [SEQ ID NO. 3]

Oligonucleotide 3
5'-GGCCG AATTC TTACA ATTTC CATTC AGGCT GCGCA ACTGT TGG-3' [SEQ ID NO. 4]

Oligonucleotides 2 and 3 (200 pmoles each) were combined with 0.1 µg PvuII-cut pGEM4 DNA (which contained the LacZ α-peptide sequence), and subjected to PCR amplification in a volume of 100 µl containing:

50 mM KCl,
10 mM Tris-HCl pH 8.3,
1.5 mM MgCl$_2$,
0.4 mM dNTPs,
0.1% gelatin, and
5 U TaqI DNA polymerase, and incubated for 30 cycles, 1 min @ 94° C., 2 mins @ 50° C., 2 mins @ 72° C.

Plasmid pGEM4 is commercially available from Promega Corporation, Madison, Wis., USA.

The amplified product of 210 base-pairs was purified using low-gelling temperature agarose electrophoresis, and was used as primer in a second round of PCR amplification.

Following the second round of PCR amplification, 2.0 µg of 210 base-pair amplified product, 200 pmoles oligonucleotide 1 and 0.1 µg 450 base-pair fragment containing the *T. thermophila* IVS were mixed and subjected to PCR amplification using the conditions shown above. The resulting 660 base-pair product was digested with the restriction endonucleases EcoRI and HindIII, and cloned into the plasmid vector pGEM4. The complete sequence of the CAT-LacZ α-peptide ribozyme DNA sequence is presented as SEQ ID NO. 5 and FIG. 3B.

The cloning vector containing the cloned sequences was transformed into, and propagated in, the bacterial host XL1/Blue (Strategene, La Jolla, Calif.), using techniques known in the art (Maniatis, *Molecular Cloning, A Laboratory Guide*, 2nd edition, 1989, Cold Spring Harbor Laboratory, Publishers). However, any bacterial host capable of stably maintaining the vector may be used, for example the JM109.

The plasmid may be extracted from the host cell for further analysis using techniques commonly known in the art (Maniatis, *Molecular Cloning, A Laboratory Guide*, 2nd edition, 1989, Cold Spring Harbor Laboratory, Publishers).

II. In vitro Transcription of Cloned Ribozyme and Target RNAs

Using standard procedures, cloned sequences were purified from the bacterial host and the plasmid linearized using a restriction endonuclease that does not cut the ribozyme sequence (for example, EcoRI), and transcribed using T7 RNA polymerase in a volume of 100 µl, containing:

5 µg linearized plasmid DNA,
40 mM Tris-HC pH 7.5,
6 mM MgCl$_2$,
2 mM spermidine,
10 mM NaCl,
10 mM DTT,
1 mM NTPs (containing 20 µCi [α-$^{32}$P]UTP, if labelled RNA transcripts were desired),
100 U RNasin, and
50 U T7 RNA polymerase, and the reaction was incubated at 37° C. for 2 hours.

RNA transcripts were purified by 5% polyacrylamide gel electrophoresis before use (TBE, 7M urea gel). RNAs containing active *T. thermophila* IVS sequences undergo some spontaneous scission at the 3' intron-exon junction during transcription. Fragments are removed by electrophoretic purification for clarity of analysis during subsequent trans-splicing assays.

III. In Vitro Trans-splicing Reaction Conditions

Target and/or trans-splicing ribozymes are incubated under the following conditions:

0.1–0.5 µg RNA component (amount depends on type of experiment, usually ribozyme in 5-fold excess of target), 30 mM Tris-HCl pH 7.5,
100 mM NaCl,
2 mM GTP,
5 mM MgCl$_2$,
in a volume of 5 µl at 42° C., 60 mins.

The reaction is diluted with 95 µl 0.1 mM Na$_2$EDTA, 200 mM NaCl, and ethanol precipated. The RNAs are then analysed on 5% polyacrylamide gels containing TBE buffer, 7M urea and 25% formamide, and autoradiographed.

IV. Assay of Endonucleolytic Activity

After base-pairing of the ribozyme and target, the first step in trans-splicing is the guanosine mediated cleavage of the target RNA at the intended 5' splice site. Annealing and trans-splicing may be performed in a buffer such as 30 mM Tris-HCl, pH 7.5, 100 mM NaCl, 5 mM MgCl$_2$, 2 mM GTP at 42° C. As the 3' splice site is dispensable for this reaction, truncated trans-splicing ribozymes should behave as highly-specific endoribonucleases. To test this activity, shortened in vitro transcripts of the CAT-LacZ α-peptide trans-splicing ribozyme described above (SEQ ID NO. 5 and FIG. 3) were incubated with CAT mRNA sequences. The CAT-LacZ ribozyme cassette is on a HindIII-EcoRI fragment. The ScaI cleavage site marks a position 5 bases upstream of the 3' splice site. The ribozyme specifically cleaved the target RNA at the expected single site to produce the expected size fragments.

V. The Trans-splicing Reaction

To confirm the ability of the CAT-LacZ α-peptide ribozyme to catalyze the ligation of 3' exon sequences at the 5' splice site, various forms were incubated with radiolabelled CAT RNA. Ribozyme transcripts were synthesized from DNA templates which had been 3' truncated at one of several positions, ranging from the end of the ribozyme core through the exon sequence. Incubation with labelled CAT led to the formation of the expected spliced products, which differed in length depending on the extent of 3' exon sequence.

In addition, a certain proportion of the CAT-LacZ α-peptide ribozyme molecules underwent spontaneous cleavage at the 3' splice site during in vitro transcription, similar to the intact T. thermophila intron. These cleaved forms, terminated at the guanosine residue adjacent the 3' splice site, were also incubated with CAT RNA. In this case, the ribozyme itself is ligated to a 3' portion of the CAT RNA, to produce a product of about 550 nucleotides in size. This reaction is similar to the self-circularization of the intact intron, and the same ligation product is found in the other trans-splicing reactions.

VI. Accuracy of the Trans-splicing

The products from a CAT-LacZ α-peptide trans-splicing reaction were reverse-transcribed, and amplified by polymerase chain reaction using two oligonucleotides complementary to sequences on either side of the predicted splice sites. Amplified sequences were cloned and sequenced. Individual recombinants showed no variation from the expected sequence of the spliced products. As found in studies with the intact intron, splicing appears to be highly accurate.

Accordingly, the studies above show that a trans-splicing ribozyme designed according to the guidelines of the invention is capable of accurate, effective trans-splicing in vitro.

Example 2

Design of a Trans-Splicing Ribozyme that Provides Plant Virus Resistance

Figure 5:
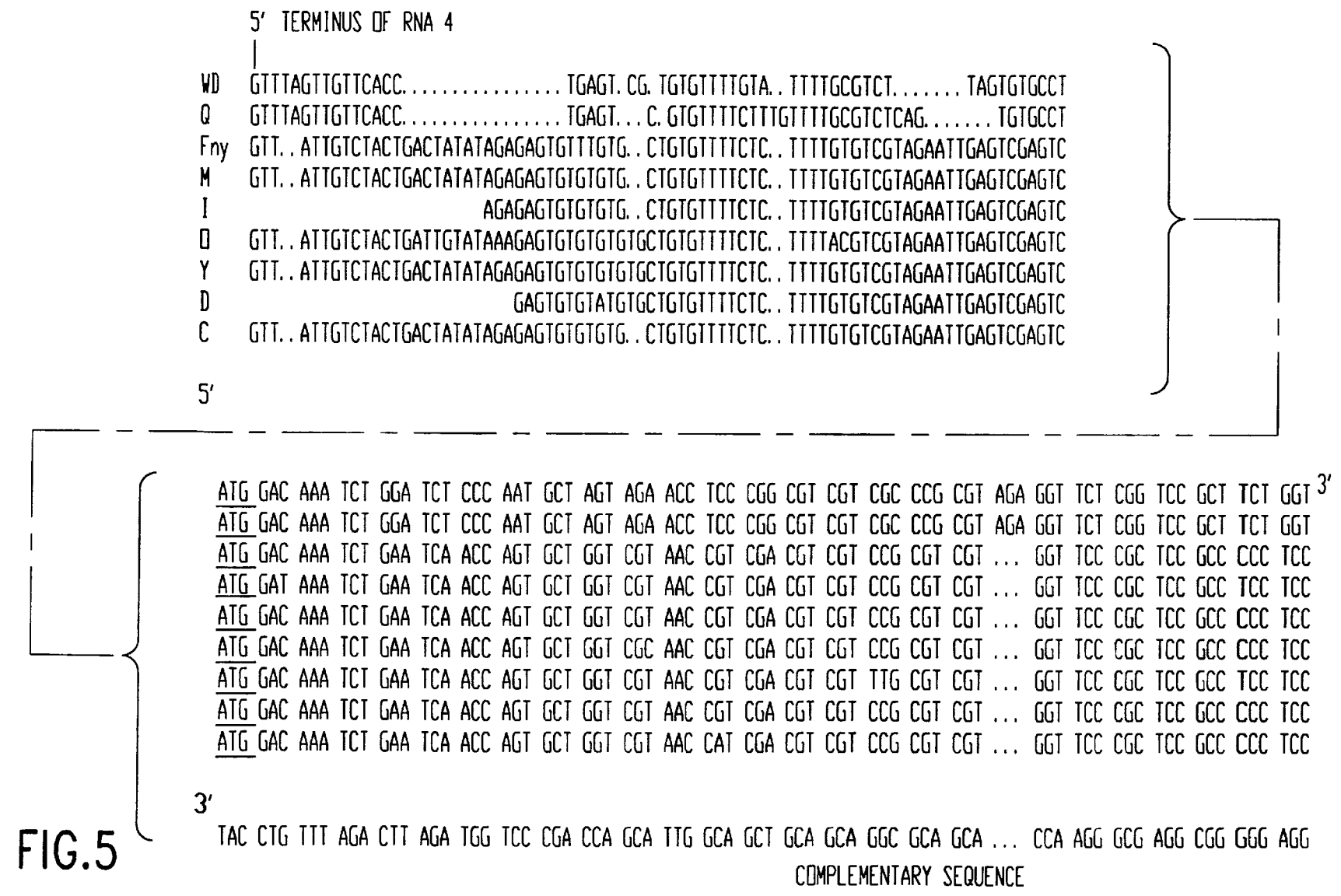

Cucumber mosaic virus (CMV) is a pandemic virus with a large number of known strains. Nine sequence strains are shown in the region of the start of their coat protein cistron encoded in RNA 3 and the subgenomic mRNA 4 (SEQ ID NOS. 7–25; FIGS. 4(A) and 5). Two sites have been chosen which are conserved in sequence and downstream from the AUG start codon of the coat protein. Oligonucleotides for the construction of ribozymes capable of trans-splicing the ile-mutant form of DTA into the CMV coat protein mRNA are shown in FIG. 4B and discussed below.

The trans-splicing ribozymes shown in FIG. 4C are targetted to the CMV virus sequences shown in FIG. 4B and will result not only in the cleavage of the CMV RNA molecules but in the expression of diphtheria toxin A-chain in the infected cell. The trans-splicing cassettes shown in FIGS. 4A–4C may be transformed into any CMV-susceptible plant species using techniques known in the art, and transgenic progeny challenged by CMV infection. The design of the ribozyme is such that virus infection is necessary to initiate toxin production via RNA trans-splicing because the ribozyme itself is not translated. The localized death of the infected cells that results from expression of the toxin could limit replication and spread of the virus within the plant giving an artificial hypersensitive response.

Example 3

Construction of Mutant Forms of DTA

The major criteria for successful design of a ribozyme that trans-splices a sequence encoding a toxic product are not only the efficient and precise catalysis of trans-splicing, but also that expression of the toxic gene does not occur in the absence of trans-splicing.

These ribozyme molecules can undergo spontaneous scission at the 3' splice site. Given the extreme toxicity of DTA, it is important that any liberated 3' exon sequences not give rise to toxic translation products. The 3' exon of DTA contained an in-frame methionine at position 13, which could conceivably give rise to a truncated but toxic polypeptide. To eliminate this possibility, the wild-type sequence (Rz-DTA$_{met}$) [SEQ ID No. 6 (DNA) and SEQ ID No. 38 (protein)] was altered from methionine at this position to isoleucine (Rz-DTA$_{ile}$) [SEQ ID No. 39] or leucine (Rz-DTA$_{leu}$) [SEQ ID No. 40] in two separate ribozyme constructions (FIG. 6A). Transformation of host cells with DTA$_{ile}$ or DTA$_{leu}$ resulted in no apparent truncated, toxic peptide in the host cell.

Example 4

Construction of Pro-ribozymes for Trans-splicing

The design and construction of catalytic RNAs (ribozyme) that can specifically cleave a targeted RNA, and splice a chosen RNA segment to the 5' portion is described above. Now novel means of constructing trans-splicing ribozymes which are conformationally disrupted, and therefore inactive, in the absence of the target RNA, are presented.

Design

Figure 8:
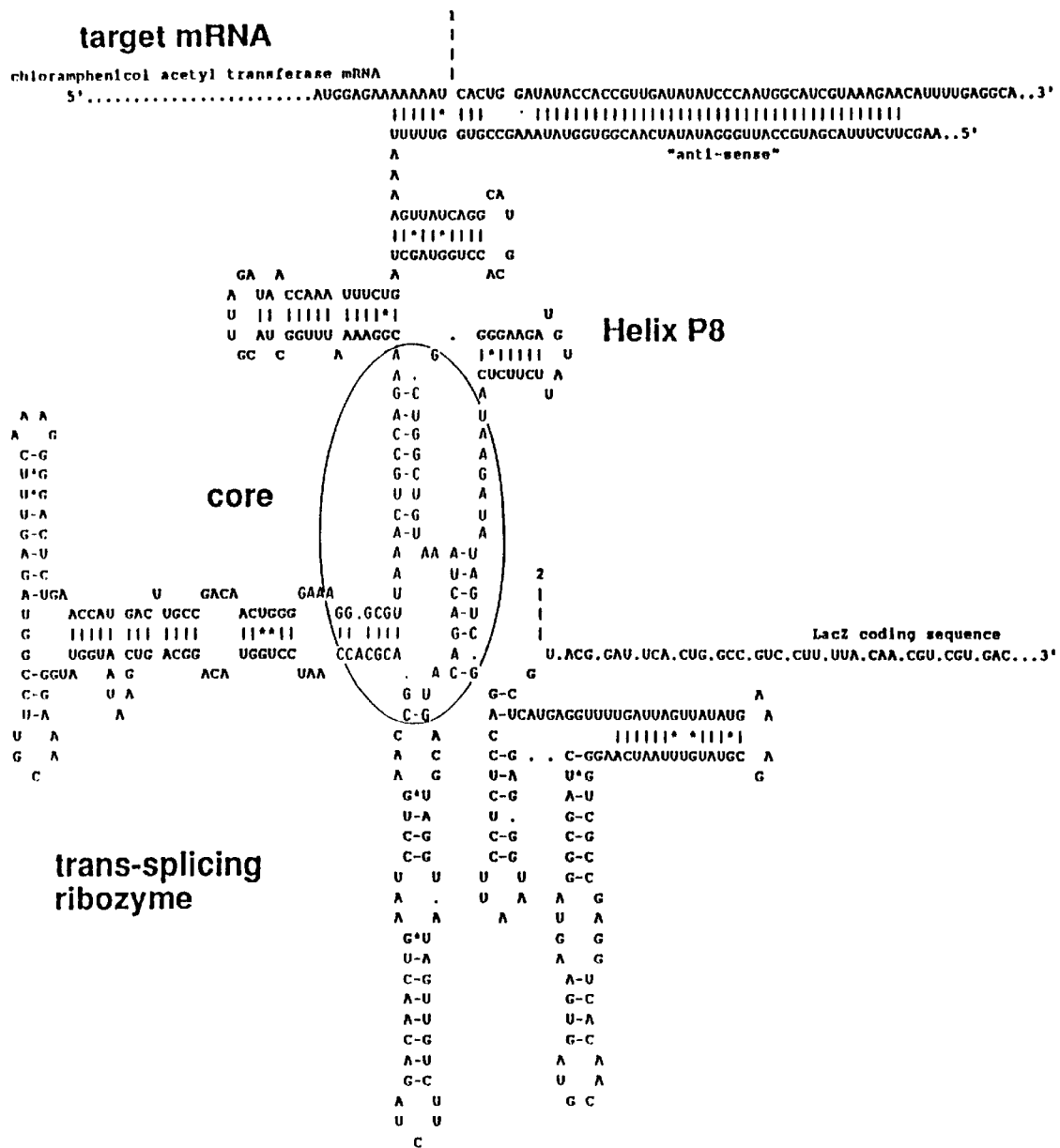
FIGS. 8, 8A and 8B show the sequence and predicted secondary structure of the CAT-LacZ trans-splicing ribozyme. Ribozyme "core" sequences-are shaded (after Cech, Gene 73:259–271 (1988)).
Figure 8A:
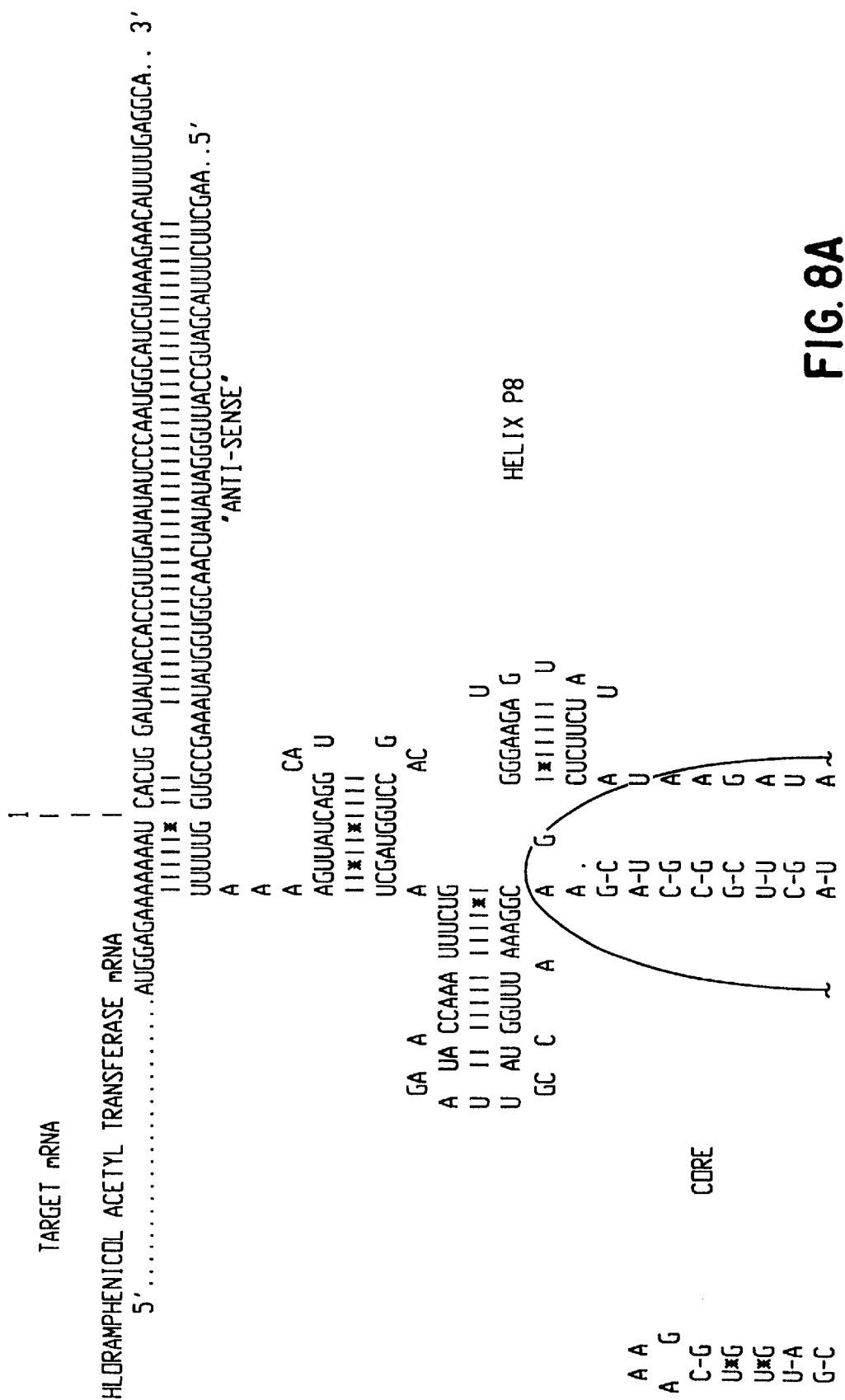
Figure 8B:
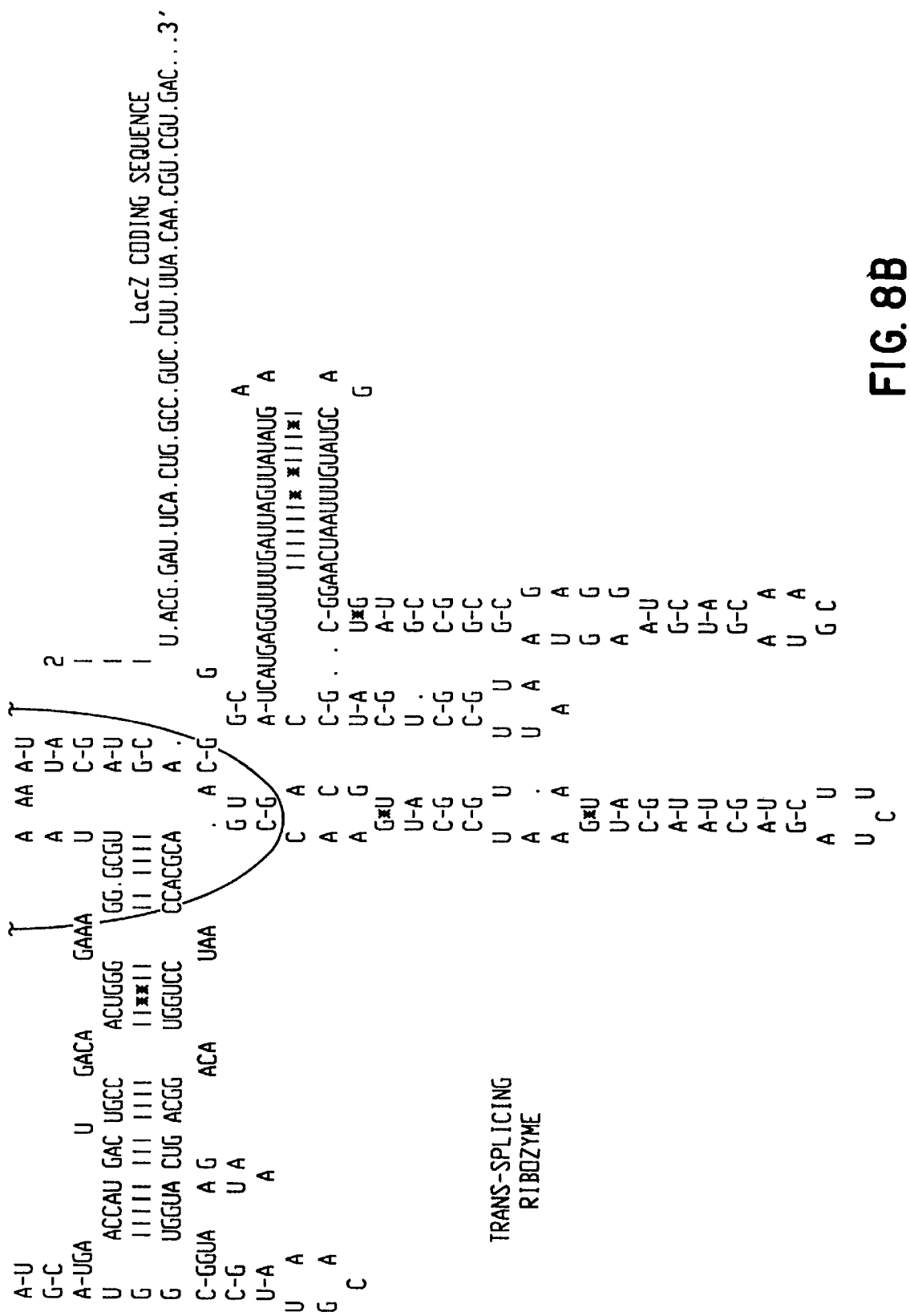
Figure 9A:
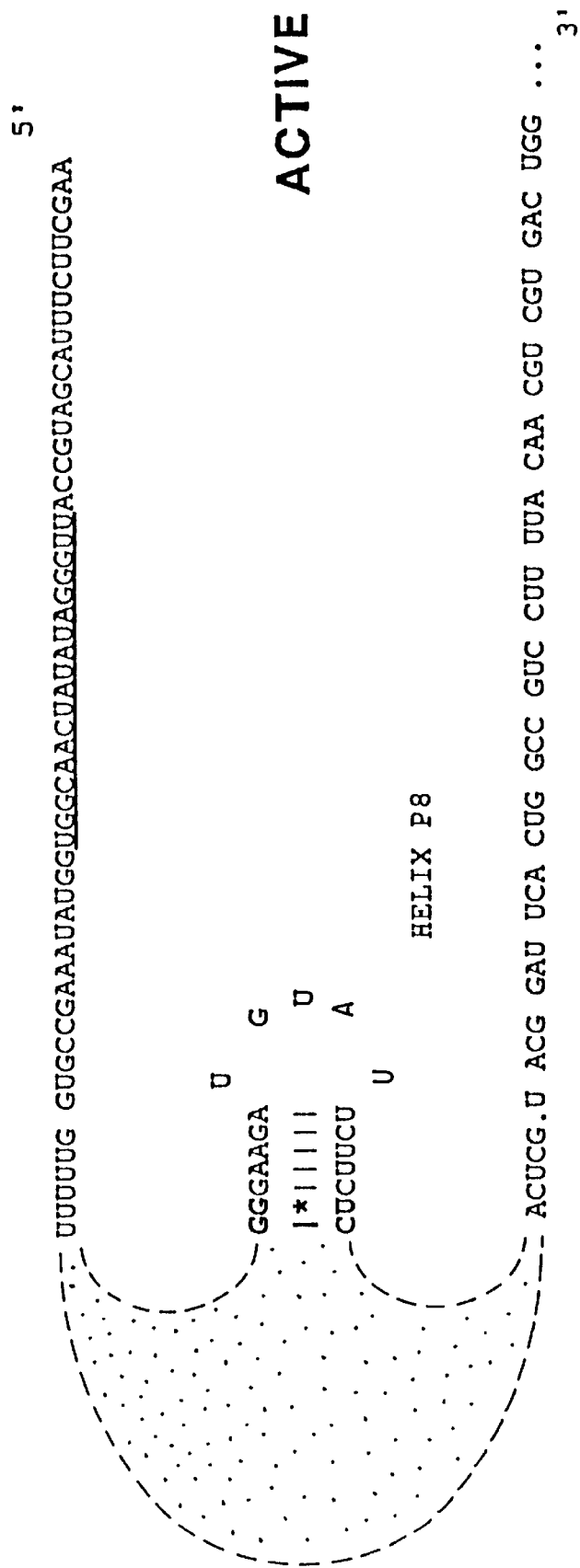
FIG. 9A shows active CAT-LacZ ribozyme shown schematically, with "antisense", ribozyme domain with helix P8 and 3' "exon" sequences.
Figure 9B:
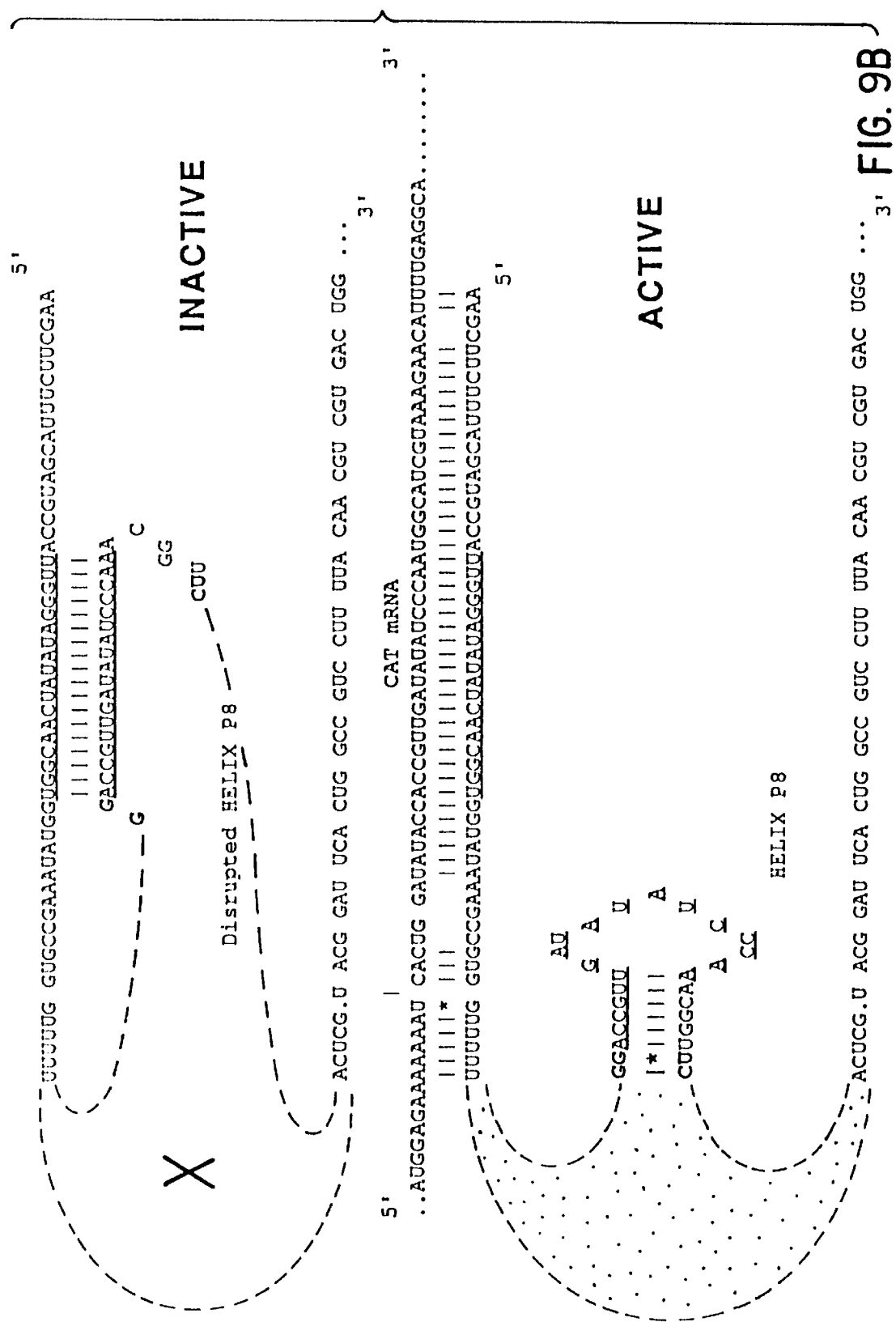
FIG. 9B, upper portion, shows inactive CAT-LacZ pro-ribozyme 2 shown with base-pairing between sequences in the modified helix P8 and the "anti-sense" region.

As a test for the design of pro-ribozymes, the CAT-LacZ trans-splicing ribozyme which described earlier was modified (FIGS. 7A–7D). Phylogenetic comparisons and mutational analysis (for review, see Cech, *Ann Rev. Biochem.* 59:543–568 (1990)) have indicated that a core region of the group I self-splicing introns is highly conserved and important for activity (FIGS. 8A–8B). For the construction of trans-splicing pro-ribozymes a helix immediately adjacent to this region, P8, was disrupted. In the first experiments, 13 or 18 nucleotides of new sequence were introduced into the 5' strand and loop of helix P8, to produce pro-ribozyme 1 and 2, respectively. The extra nucleotides were complementary to the 5' "anti-sense" portion of the ribozyme, while the flanking sequences were adjusted to conserve (1) the actual sequences at the base of P8, and (2) the extent of base-pairing possible within P8 (FIG. 8C). The extent of self-complementarity between the sequences inserted into helix P8 and the 5' "anti-sense" region of the pro-ribozyme is such that this new helix would be expected to form in nascent transcripts, in preference to helix P8. The formation of this alternative helix would also be expected to disrupt flanking secondary and perhaps tertiary interactions within the catalytic core of the ribozyme. Thus, mis-folding of the pro-ribozyme would render it catalytically inactive (FIG. 9B). However, base-pairing of the pro-ribozyme with the intended target RNA would displace the P8-"anti-sense" base-pairing, sequester the "anti-sense" sequences and allow re-formation of the P8 helix and an active catalytic domain. Displacement of the P8-"anti-sense" helix results in a greater sum of base-pairs and allows proper folding of the catalytic domain, so should be energetically favored.

CAT-LacZ pro-ribozymes

Figure 10:
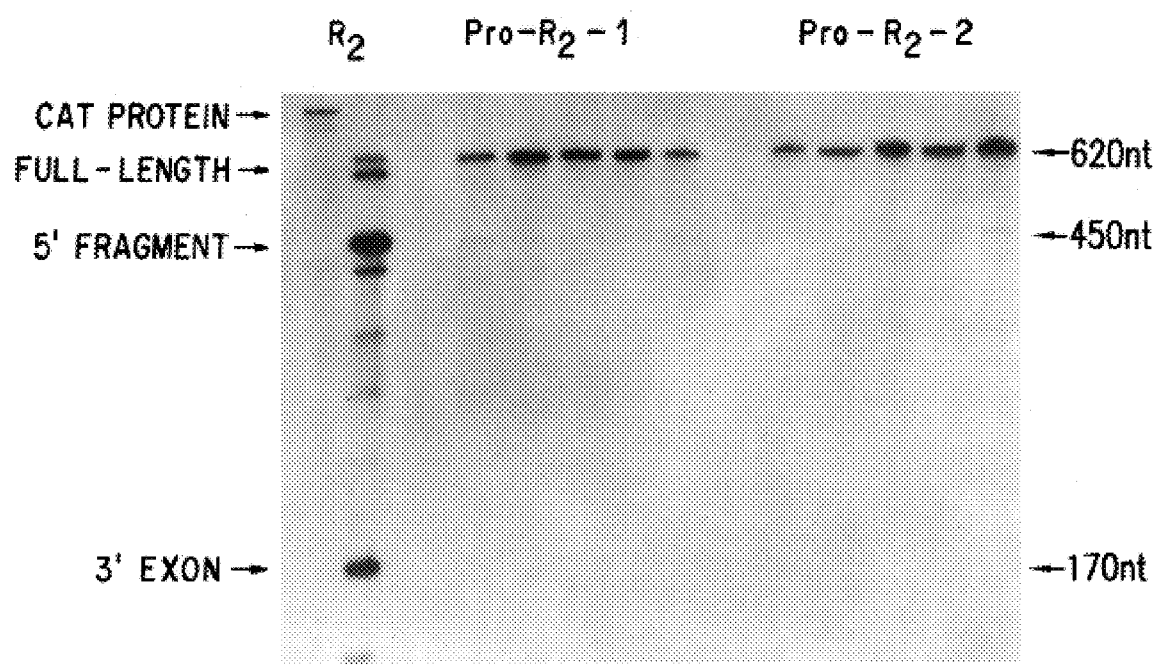
FIG. 10 shows stability of CAT-LacZ pro-ribozyme transcripts. Plasmids containing the CAT-LacZ ribozyme and pro-ribozyme sequences were cleaved with EcoRI and transcribed using T7 or SP6 RNA polymerase and [32-P]UTP. Radiolabeled transcripts were fractionated by 5% polyacrylamide gel electrophoresis in 7M urea and 25% formamide, and autoradiographed. The ribozyme transcripts underwent extensive hydrolysis, primarily at the "3' exon" junction. The pro-ribozyme forms were markedly less reactive.
Figure 11:
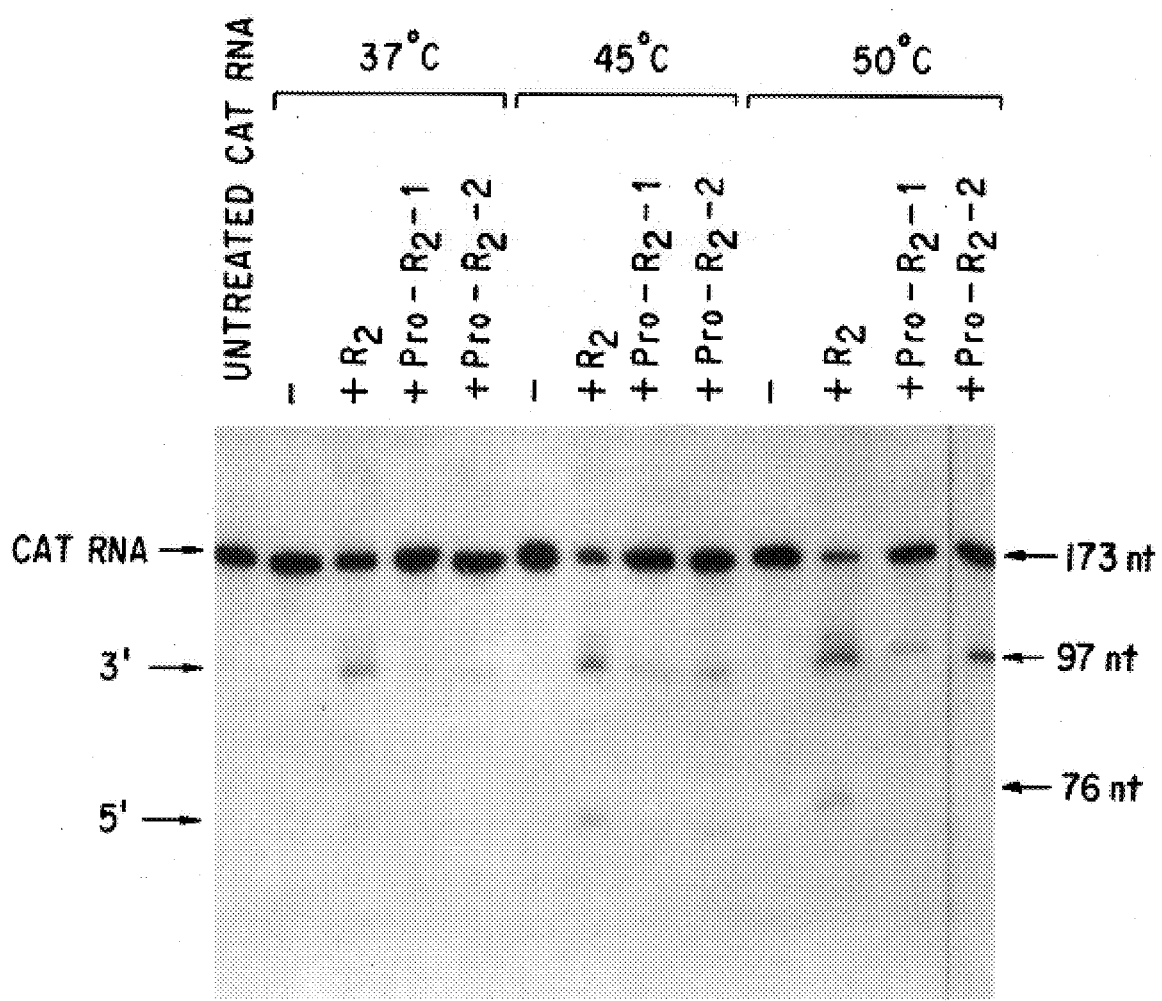
FIG. 11 shows endoribonuclease activity of CAT-LacZ pro-ribozymes. Plasmids containing CAT-LacZ ribozyme and pro-ribozyme sequences were cleaved, with ScaI, and transcribed with T7 or SP6 RNA polymerase. Transcripts were incubated for 30' at 37° C., 45° C. and 50° C. in 40 mM Tris-HCl pH 7.5, 6 mM $MgCl_2$, 2 mM spermidine, 10 mM NaCl, 2 mM GTP with radiolabeled CAT RNA, transcribed using T7 RNA polymerase from plasmid cut with PuvII. Products were fractionated by 5% polyacrylamide gel electrophoresis in 7M urea and 25% formamide, and autoradiographed. RNA mediated cleavage of the 173 nt (nucleotides) CAT RNA produces 5' and 3' fragments of 76 nt and 97 nt, respectively.

Cloned sequences corresponding to the two CAT-LacZ pro-ribozymes were constructed using PCR-mutagenesis as described above, and RNAs were produced by in vitro transcription. The CAT-LacZ trans-splicing ribozyme was observed to undergo scission during transcription at the 3' splice junction, as a result of hydrolysis catalyzed by the intron sequences. Similar hydrolysis is seen in in vitro transcripts of the unmodified *Tetrahymena thermophila* intron. In contrast, transcripts of the different CAT-LacZ pro-ribozymes are more stable, with little cleavage evident under the same conditions (FIG. 10). This indicates that the pro-ribozymes are inactive, which would be expected if the catalytic sequences were mis-folded. Truncated forms of the pro-ribozymes were tested for specific endoribonuclease activity directed against the CAT RNA. CAT-LacZ pro-ribozyme RNAs were transcribed from templates truncated at the ScaI site, to remove the 3' splice junction and LacZ sequences. Both ribozyme and pro-ribozyme RNAs are stable after removal of the 3' splice site. Incubation of the truncated pro-ribozymes with CAT RNA led to specific cleavage of the target RNA to give fragments of the expected sizes (FIG. 11). Specific cleavage activity was seen at 37, 45 and 50 degrees.

Figure 13:
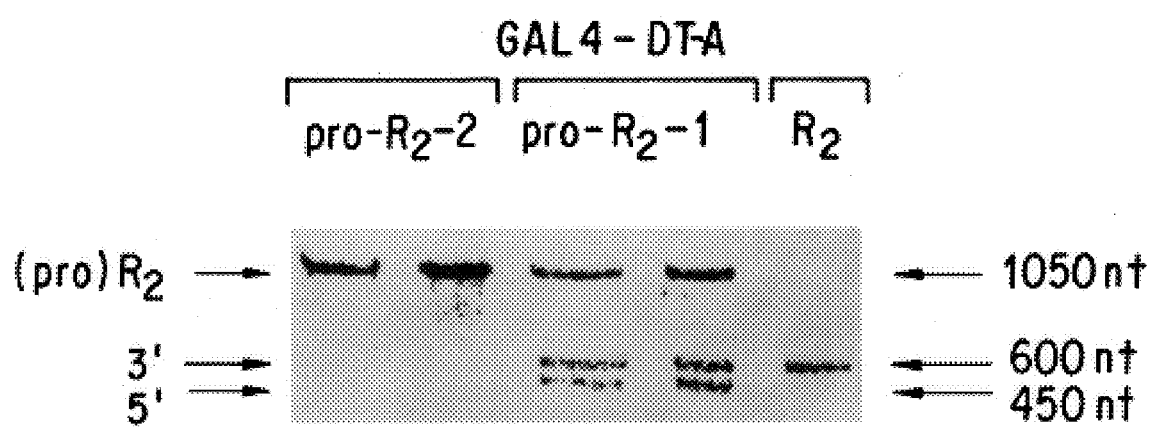
FIG. 13 shows the stability of GAL4-DTA pro-ribozymes. Plasmids containing ribozyme and pro-ribozyme sequences were linearized with XhoI and transcribed using T7 RNA polymerase. Transcripts were incubated for 60' at 50° C. n 40 mM Tris-HCl pH 7.5, 6 mM $MgCl_2$, 2 mM spermidine, 10 mM NaCl, 1 mM GTP, were fractionated by 5% polyacrylamide gel electrophoresis in 7M urea and 25% formamide, and autoradiographed. Ribozyme transcripts are extensively hydrolysed under these conditions, while pro-ribozyme 1 is less so and pro-ribozyme 2 is stable.

Pro-ribozyme forms of the GAL4-DTA trans-splicing ribozyme were also constructed (FIG. 12). Regions of 20 nucleotides (complementary to the "anti-sense" region) were inserted into the 5' strand and loop of helix P8. The two pro-ribozymes differed in the extent of base-pairing possible in the modified helices P8, and GAL4-DTA pro-ribozyme 1 possessing both a longer stem and fewer (3) accessible bases in the loop. The helix P8 of GAL4-DTA pro-ribozyme 2 more closely resembles that of the CAT-LacZ pro-ribozyme 2, with a larger loop (14 bases) containing sequences complementary to the "anti-sense" region. Transcripts of the GAL4-DTA pro-ribozymes are more stable than those of the unmodified ribozyme. In particular, pro-ribozyme 2 is mainly intact after incubation in conditions that result in essentially complete self-cleavage of the ribozyme form (30'@50° C., 10 mM $MgCl_2$, 2 mM GTP, see FIG. 13).

Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A first polynucleotide molecule, said polynucleotide molecule comprising a sequence encoding a trans-splicing ribozyme, said ribozyme being capable of trans-splicing a desired RNA sequence into a target RNA sequence in vitro or in vivo, said ribozyme comprising sequences complementary to said target mRNA sequence.

2. A polynucleotide molecule, said molecule comprising a sequence encoding a trans-splicing ribozyme, the sequence of said ribozyme comprising a fusion RNA, such fusion RNA providing (1) a first RNA sequence, said first RNA sequence being sufficient for targeting said ribozyme to hybridize to a target RNA, and (2) a second RNA sequence, said second RNA sequence being capable of being transferred colinearly into a target RNA as a result of the trans-splicing activity of said ribozyme.

3. The polynucleotide molecule of claim 2, wherein said second RNA sequence comprises a sequence that encodes a peptide toxic to a host cell.

4. The polynucleotide molecule of claim 3, wherein said peptide is a DTA peptide.

5. The polynucleotide molecule of claim 4, wherein said DTA peptide is a mutant peptide sequence.

6. The polynucleotide molecule of claim 5, wherein said mutant peptide sequence comprises amino acids encoded by SEQ ID. No. 39.

7. The polynucleotide molecule of claim 5, wherein said mutant peptide sequence comprises amino acids encoded by SEQ ID. No. 40.

8. The polynucleotide molecule of claim 1, wherein said molecule is RNA.

9. The polynucleotide molecule of claim 1, wherein said molecule is DNA.

10. A polynucleotide molecule comprising a ribozyme expression cassette, said cassette being capable of being stably inserted into the genome of a host, and said cassette comprising the sequence of a promoter capable of functioning in such host, operably-linked to the coding sequence of the polynucleotide of claim 1.

11. A host cell comprising the polynucleotide molecule of claim 10.

12. The host cell of claim 11, wherein said host cell is a viral cell.

13. The host cell of claim 11, wherein said host cell is a prokaryotic cell.

14. The host cell of claim 11, wherein said host cell is a eukaryotic cell.

15. The host cell of claim 14, wherein said eukaryotic cell is a plant cell.

16. The host cell of claim 14, wherein said eukaryotic cell is an animal cell.

17. The host cell of claim 16, wherein said animal is a mammal.

18. The host cell of claim 17, wherein said animal is human.

19. A method for in vitro trans-splicing, such method comprising the steps of:
 (1) providing the polynucleotide molecule of claim 1 in a trans-splicing reaction mixture, said polynucleotide comprising a sequence capable of hybridizing with a second polynucleotide;
 (2) providing said second polynucleotide to such reaction mixture; and
 (4) catalyzing the trans-splicing of said second polynucleotide under said conditions.

20. A method for in vivo trans-splicing, said method comprising the steps of:
 (1) providing a polynucleotide of claim 8 to a host cell;
 (2) expressing said ribozyme encoded by said molecule in said host cell;
 (3) expressing a substrate of said ribozyme in said host cell; and
 (4) catalyzing the trans-splicing of said ribozyme with such substrate in said host cell.

21. A method for inactivating the activity of a target RNA, said method comprising:
 (1) providing the polynucleotide of claim 1 to a trans-splicing reaction mixture, said ribozyme possessing catalytic activity against a target RNA, said catalytic activity resulting in the inactivation of the functioning of said target RNA;
 (2) providing said target RNA to said mixture; and
 (3) providing conditions that allow said polynucleotide to express said catalytic activity.

22. A method for providing a desired genetic sequence to a host cell in vivo, said method comprising:
 (1) providing the polynucleotide of claim 8 to said host cell, said polynucleotide possessing catalytic activity against a target RNA in said host cell, said ribozyme being capable of trans-splicing said desired genetic sequence;
 (2) providing said target RNA in said host cell; and
 (3) providing conditions that allow said ribozyme to trans-splice said desired genetic sequence into the sequence of said target RNA.

23. A method for engineering male or female sterility in a plant, said method comprising providing the polynucleotide of claim 8 to a germ cell of said species, said ribozyme being targeted to an RNA that, when expressed as a protein, is necessary for the fertility of said plant.

24. A method of conferring a desired genetic trait in a plant, said method comprising providing a germ cell of said plant with the polynucleotide of claim 8, said ribozyme encoding a trans-splicing sequence capable of conferring said desired genetic trait in said plant.

25. A method for immunizing plants against a plant pathogen, said method comprising the transforming plant cells with the polynucleotide of claim 8, wherein said polynucleotide encodes a trans-splicing sequence capable of providing immunity to said pathogen to said plant.

26. The method of claim 25, wherein said pathogen is cucumber mosaic virus.

27. A method for construction of a pro-ribozyme, wherein said method comprises disruption of helix P8.

28. The method of claim 27, wherein said disruption is caused by P8-anti-sense base-pairing.

29. The polynucleotide molecule of claim 1 wherein said ribozyme is a pro-ribozyme.

30. The polynucleotide molecule of any one of claim 8 wherein said ribozyme is a pro-ribozyme.

31. The polynucleotide molecule of any one of claim 9 wherein said ribozyme is a pro-ribozyme.

32. The polynucleotide molecule of any one of claim 10 wherein said ribozyme is a pro-ribozyme.

33. The host cell of claim 11, wherein said ribozyme is a pro-ribozyme.

34. The method of claim 19, wherein said ribozyme is a pro-ribozyme.

35. The method of claim 20, wherein said ribozyme is a pro-ribozyme.

36. The method of claim 21, wherein said ribozyme is a pro-ribozyme.

37. The method of claim 22, wherein said ribozyme is a pro-ribozyme.

38. The method of claim 23, wherein said ribozyme is a pro-ribozyme.

39. The method of claim 24, wherein said ribozyme is a pro-ribozyme.

40. The method of claim 25, wherein said ribozyme is a pro-ribozyme.

* * * * *

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
      (A) LENGTH: 517 base pairs
      (B) TYPE: nucleic acid
      (C) STRANDEDNESS: both
      (D) TOPOLOGY: both (xi) SEQUENCE DESCRIPTION: SEQ ID NO:1:

```
TGACGCAATT CAACCAAGCG CGGGTAAACG GCGGGAGTAA CTATGACTCT CTAAATAGCA      60

ATATTTACCT TTGGAGGGAA AAGTTATCAG GCATGCACCT CCTAGCTAGT CTTTAAACCA     120

ATAGATTGCA TCGGTTTAAA AGGCAAGACC GTCAAATTGC GGGAAAGGGG TCAACAGCCG     180

TTCAGTACCA AGTCTCAGGG GAAACTTTGA CATGGCCTTG CAAAGGGTAT GGTAATAAGC     240

TGACGGACAT GGTCCTAACC ACGCAGCCAA GTCCTAAGTC AACAGATCTT CTGTTGATAT     300

GGATGCAGTT CACAGACTAA ATGTCGGTCG GGGAAGATGT ATTCTTCTCA TAAGATATAG     360

TCGGACCTCT CCTTAATGGG AGGTAGCGGA TGAATGGATG CAACACTGGA GCCGCTGGGA     420

ACTAATTTGT ATGCGAAAGT ATATTGATTA GTTTTGGAGT ACTCGTAAGG TAGCCAAATG     480

CCTCGTCATC TAATTAGTGA CGCGCATGAA TGGATTA                              517
```

(2) INFORMATION FOR SEQ ID NO:2:

(i) SEQUENCE CHARACTERISTICS:
        (A) LENGTH: 82 base pairs
        (B) TYPE: nucleic acid
        (C) STRANDEDNESS: both
        (D) TOPOLOGY: both (xi) SEQUENCE DESCRIPTION: SEQ ID NO:2:

```
GGCCAAGCTT CTTTACGATG CCATTGGGAT ATATCAACGG TGGTATAAAC CCGTGGTTTT      60

TAAAAGTTAT CAGGCATGCA CC                                              82
```

(2) INFORMATION FOR SEQ ID NO:3:

(i) SEQUENCE CHARACTERISTICS:
        (A) LENGTH: 47 base pairs
        (B) TYPE: nucleic acid
        (C) STRANDEDNESS: both
        (D) TOPOLOGY: both (xi) SEQUENCE DESCRIPTION: SEQ ID NO:3:

```
GATTAGTTTT GGAGTACTCG TACGGATTCA CGGCCGTCGT TTTACAA                   47
```

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: both
        (D) TOPOLOGY: both (xi) SEQUENCE DESCRIPTION: SEQ ID NO:4:

```
GGCCGAATTC TTACAATTTC CATTCAGGCT GCGCAACTGT TGG                       43
```

(2) INFORMATION FOR SEQ ID NO:5:

(i) SEQUENCE CHARACTERISTICS:
        (A) LENGTH: 623 base pairs
        (B) TYPE: nucleic acid
        (C) STRANDEDNESS: both
        (D) TOPOLOGY: both (xi) SEQUENCE DESCRIPTION: SEQ ID NO:5:

```
GGGAGACCGG AAGCTTCTTT ACGATGCCAT TGGGATATAT CAACGGTGGT ATAAAGCCGT      60

GGTTTTTAAA AGTTATCAGG CATGCACCTG GTAGCTAGTC TTTAAACCAA TAGATTGCAT     120

CGGTTTAAAA GGCAAGACCG TCAAATTGCG GGAAAGGGGT CAACAGCCGT TCAGTACCAA     180

GTCTCAGGGG AAACTTTGAG ATGGCCTTGC AAAGGGTATG GTAATAAGCT GACGGACATG     240

GTCCTAACCA CGCAGCCAAG TCCTAAGTCA ACAGATCTTC TGTTGATATG GATGCAGTTC     300

ACAGACTAAA TGTCGGTCGG GGAAGATGTA TTCTTCTCAT AAGATATAGT CGGACCTCTC     360

CTTAATGGGA GCTAGCGGAT GAAGTGATGC AACACTGGAG CCGCTGGGAA CTAATTTGTA     420

TGCGAAAGTA TATTGATTAG TTTTGGAGTA CTCGTACGGA TTCACTGGCC GTCGTTTTAC     480

AACGTCGTGA CTGGGAAAAC CCTGGCGTTA CCCAACTTAA TCGCCTTGCA GCACATCCCC     540

CTTTCGCCAG CTGGCGTAAT AGCGAAGAGG CCCGCACCGA TCGCCCTTCC CAACAGTTGC     600

GCAGCCTGAA TGGAAATTGT AAG                                            623
```

(2) INFORMATION FOR SEQ ID NO:6:

(i) SEQUENCE CHARACTERISTICS:
        (A) LENGTH: 70 base pairs
        (B) TYPE: nucleic acid
        (C) STRANDEDNESS: both (D) TOPOLOGY: both (xi) SEQUENCE DESCRIPTION: SEQ ID NO:6:

TCTCGATGAT GTTGTTGATT CTTCTAAATC TTTTGTGATG GAAAACTTTT CTTCGTACCA      60

CGGGACTAAA                                                            70

(2) INFORMATION FOR SEQ ID NO:7:

(i) SEQUENCE CHARACTERISTICS:
        (A) LENGTH: 134 base pairs
        (B) TYPE: nucleic acid
        (C) STRANDEDNESS: both
        (D) TOPOLOGY: both (xi) SEQUENCE DESCRIPTION: SEQ ID NO:7:

GTTTAGTTGT TCACCTGAGT CGTGTGTTTT GTATTTTGCG TCTTAGTGTG CCTATGGACA      60

AATCTGGATC TCCCAATGCT AGTAGAACCT CCCGGCGTCG TCGCCCGCGT AGAGGTTCTC     120

GGTCCGCTTC TGGT                                                      134

(2) INFORMATION FOR SEQ ID NO:8:

(i) SEQUENCE CHARACTERISTICS:
        (A) LENGTH: 134 base pairs
        (B) TYPE: nucleic acid
        (C) STRANDEDNESS: both
        (D) TOPOLOGY: both (xi) SEQUENCE DESCRIPTION: SEQ ID NO:8:

GTTTAGTTGT TCACCTGAGT CGTGTTTTCT TTGTTTTGCG TCTCAGTGTG CCTATGGACA      60

AATCTGGATC TCCCAATGCT AGTAGAACCT CCCGGCGTCG TCGCCCGCGT AGAGGTTCTC     120

GGTCCGCTTC TGGT                                                      134

(2) INFORMATION FOR SEQ ID NO:9:

(i) SEQUENCE CHARACTERISTICS:
        (A) LENGTH: 152 base pairs
        (B) TYPE: nucleic acid
        (C) STRANDEDNESS: both
        (D) TOPOLOGY: both (xi) SEQUENCE DESCRIPTION: SEQ ID NO:9:

GTTATTGTCT ACTGACTATA TAGAGAGTGT TTGTGCTGTG TTTTCTCTTT TGTGTCGTAG      60

AATTGAGTCG AGTCATGGAC AAATCTGAAT CAACCAGTGC TGGTCGTAAC CGTCGACGTC     120

GTCCGCGTCG TGGTTCCCGC TCCGCCCCCT CC                                  152

(2) INFORMATION FOR SEQ ID NO:10:

(i) SEQUENCE CHARACTERISTICS:
        (A) LENGTH: 152 base pairs
        (B) TYPE: nucleic acid
        (C) STRANDEDNESS: both
        (D) TOPOLOGY: both (xi) SEQUENCE DESCRIPTION: SEQ ID NO:10:

GTTATTGTCT ACTGACTATA TAGAGAGTGT GTGTGCTGTG TTTTCTCTTT TGTGTCGTAG      60

AATTGAGTCG AGTCATGGAT AAATCTGAAT CAACCAGTGC TGGTCGTAAC CGTCGACGTC     120

GTCCGCGTCG TGGTTCCCGC TCCGCCTCCT CC                                  152

(2) INFORMATION FOR SEQ ID NO:11:

(i) SEQUENCE CHARACTERISTICS:

(A) LENGTH: 131 base pairs
        (B) TYPE: nucleic acid
        (C) STRANDEDNESS: both
        (D) TOPOLOGY: both (xi) SEQUENCE DESCRIPTION: SEQ ID NO:11:

AGAGAGTGTG TGTGCTGTGT TTTCTCTTTT GTGTCGTAGA ATTGAGTCGA GTCATGGACA         60

AATCTGAATC AACCAGTGCT GGTCGTAACC GTCGACGTCG TCCGCGTCGT GCTTCCCGCT        120

CCGCCCCCTC C                                                             131

(2) INFORMATION FOR SEQ ID NO:12:

(i) SEQUENCE CHARACTERISTICS:
        (A) LENGTH: 154 base pairs
        (B) TYPE: nucleic acid
        (C) STRANDEDNESS: both
        (D) TOPOLOGY: both (xi) SEQUENCE DESCRIPTION: SEQ ID NO:12:

GTTATTGTCT ACTGATTGTA TAAAGAGTGT GTGTGTGCTG TGTTTTCTCT TTTACGTCGT         60

AGAATTGAGT CGAGTCATGG ACAAATCTGA ATCAACCAGT GCTGGTCGCA ACCGTCGACG        120

TCGTCCGCGT CGTGGTTCCC GCTCCGCCCC CTCC                                    154

(2) INFORMATION FOR SEQ ID NO:13:

(i) SEQUENCE CHARACTERISTICS:
        (A) LENGTH: 154 base pairs
        (B) TYPE: nucleic acid
        (C) STRANDEDNESS: both
        (D) TOPOLOGY: both (xi) SEQUENCE DESCRIPTION: SEQ ID NO:13:

GTTATTGTCT ACTGACTATA TAGAGAGTGT GTGTGTGCTG TGTTTTCTCT TTTGTGTCGT         60

AGAATTGAGT CGAGTCATGG ACAAATCTGA ATCAACCAGT GCTGGTCGTA ACCGTCGACG        120

TCGTTTGCGT CGTGGTTCCC GCTCCGCCTC CTCC                                    154

(2) INFORMATION FOR SEQ ID NO:14:

(i) SEQUENCE CHARACTERISTICS:
        (A) LENGTH: 130 base pairs
        (B) TYPE: nucleic acid
        (C) STRANDEDNESS: both
        (D) TOPOLOGY: both (xi) SEQUENCE DESCRIPTION: SEQ ID NO:14:

GAGTGTGTAT GTGCTGTGTT TTCTCTTTTG TGTCGTAGAA TTGAGTCGAG TCATGGACAA         60

ATCTGAATCA ACCAGTGCTG GTCGTAACCG TCGACGTCGT CCGCGTCGTG GTTCCCCCTC        120

CGCCCCCTCC                                                               130

(2) INFORMATION FOR SEQ ID NO:15:

(i) SEQUENCE CHARACTERISTICS:
        (A) LENGTH: 152 base pairs
        (B) TYPE: nucleic acid
        (C) STRANDEDNESS: both
        (D) TOPOLOGY: both (xi) SEQUENCE DESCRIPTION: SEQ ID NO:15:

GTTATTGTCT ACTGACTATA TAGAGAGTGT GTGTGCTGTG TTTTCTCTTT TGTGTCGTAG         60

AATTGAGTCG AGTCATGGAC AAATCTGAAT CAACCAGTGC TGGTCGTAAC CATCGACGTC        120

GTCCGCGTCG TGGTTCCCGC TCCGCCCCCT CC                                      152

(2) INFORMATION FOR SEQ ID NO:16:

(i) SEQUENCE CHARACTERISTICS:
        (A) LENGTH: 78 base pairs
        (B) TYPE: nucleic acid
        (C) STRANDEDNESS: both
        (D) TOPOLOGY: both (xi) SEQUENCE DESCRIPTION: SEQ ID NO:16:

```
GGAGGGGGCG GAGCGGGAAC CACGACGCGG ACGACGTCGA CGGTTACGAC CAGCCCTGGT      60

AGATTCAGAT TTGTCCAT                                                    78
```

(2) INFORMATION FOR SEQ ID NO:17:

(i) SEQUENCE CHARACTERISTICS:
        (A) LENGTH: 49 base pairs
        (B) TYPE: nucleic acid
        (C) STRANDEDNESS: both
        (D) TOPOLOGY: both (xi) SEQUENCE DESCRIPTION: SEQ ID NO:17:

```
TTTGCGTCTT AGTGTGCCTA TGGACAAATC TGGATCTCCC AATGCTAGT                  49
```

(2) INFORMATION FOR SEQ ID NO:18:

(i) SEQUENCE CHARACTERISTICS:
        (A) LENGTH: 49 base pairs
        (B) TYPE: nucleic acid
        (C) STRANDEDNESS: both
        (D) TOPOLOGY: both (xi) SEQUENCE DESCRIPTION: SEQ ID NO:18:

```
TTTGCGTCTC AGTGTGCCTA TGGACAAATC TGGATCTCCC AATGCTAGT                  49
```

(2) INFORMATION FOR SEQ ID NO:19:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:19:

```
TTTGTGTCGT AGAATTGAGT CGAGTCATGG ACAAATCTGA ATCAACCAGT GCTGGT          56
```

(2) INFORMATION FOR SEQ ID NO:20:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:20:

```
TTTGTGTCGT AGAATTGAGT CGAGTCATGG ATAAATCTGA ATCAACCAGT GCTGGT          56
```

(2) INFORMATION FOR SEQ ID NO:21:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:21:

```
TTTGTGTCGT AGAATTGAGT CGAGTCATGG ACAAATCTGA ATCAACCAGT GCTGGT          56
```

(2) INFORMATION FOR SEQ ID NO:22:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:22:

TTTACGTCGT AGAATTGAGT CGAGTCATGG ACAAATCTGA ATCAACCAGT GCTGGT      56

(2) INFORMATION FOR SEQ ID NO:23:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:23:

TTTGTGTCGT AGAATTGAGT CGAGTCATGG ACAAATCTGA ATCAACCAGT GCTGGT      56

(2) INFORMATION FOR SEQ ID NO:24:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:24:

TTTGTGTCGT AGAATTGAGT CGAGTCATGG ACAAATCTGA ATCAACCAGT GCTGGT      56

(2) INFORMATION FOR SEQ ID NO:25:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:25:

TTTGTGTCGT AGAATTGAGT CGAGTCATGG ACAAATCTGA ATCAACCAGT GCTGGT      56

(2) INFORMATION FOR SEQ ID NO:26:

(i) SEQUENCE CHARACTERISTICS:
        (A) LENGTH: 59 base pairs
        (B) TYPE: nucleic acid
        (C) STRANDEDNESS: both
        (D) TOPOLOGY: both (xi) SEQUENCE DESCRIPTION: SEQ ID NO:26:

AATTTTGTGT CGTAGAATTG AGTCGAGTCA TGGACAAATC TGAATCAACC AGTGCTGCA      59

(2) INFORMATION FOR SEQ ID NO:27:

(i) SEQUENCE CHARACTERISTICS:
        (A) LENGTH: 51 base pairs
        (B) TYPE: nucleic acid
        (C) STRANDEDNESS: both
        (D) TOPOLOGY: both (xi) SEQUENCE DESCRIPTION: SEQ ID NO:27:

GCACTGGTTG ATTCAGATTT GTCCATGACT CGACTCAATT CTACGACACA A      51

(2) INFORMATION FOR SEQ ID NO:28:

(i) SEQUENCE CHARACTERISTICS:
        (A) LENGTH: 59 base pairs
        (B) TYPE: nucleic acid
        (C) STRANDEDNESS: both
        (D) TOPOLOGY: both (xi) SEQUENCE DESCRIPTION: SEQ ID NO:28:

```
AATTTTGTGT CGTAGAATTG AGTCGAGTCA TGGACAAATC TGAATCAACC AGTGCTGCA        59
```

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: both
        (D) TOPOLOGY: both (xi) SEQUENCE DESCRIPTION: SEQ ID NO:29:

```
AGCATTGGTA TCATCAGGTT TGT                                              23
```

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: both
        (D) TOPOLOGY: both (xi) SEQUENCE DESCRIPTION: SEQ ID NO:30:

```
GTTGATGATG TTGTTGATTC T                                                21
```

(2) INFORMATION FOR SEQ ID NO:31:

(i) SEQUENCE CHARACTERISTICS:
        (A) LENGTH: 10 amino acids
        (B) TYPE: amino acid
        (D) TOPOLOGY: both (xi) SEQUENCE DESCRIPTION: SEQ ID NO:31:

```
Met Asp Lys Phe Asp Asp Val Val Asp Ser
1               5                   10
```

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: both
        (D) TOPOLOGY: both (xi) SEQUENCE DESCRIPTION: SEQ ID NO:32:

```
ATGGACAAAT TGATGATGT TGTTGATTCT                                        30
```

(2) INFORMATION FOR SEQ ID NO:33:

(i) SEQUENCE CHARACTERISTICS:
        (A) LENGTH: 59 base pairs
        (B) TYPE: nucleic acid
        (C) STRANDEDNESS: both
        (D) TOPOLOGY: both (xi) SEQUENCE DESCRIPTION: SEQ ID NO:33:

```
AATTTTGTGT CGTAGAATTG AGTCGAGTCA TGGACAAATC TGAATCAACC AGTGCTGCA        59
```

(2) INFORMATION FOR SEQ ID NO:34:

(i) SEQUENCE CHARACTERISTICS:
        (A) LENGTH: 17 base pairs
        (B) TYPE: nucleic acid
        (C) STRANDEDNESS: both
        (D) TOPOLOGY: both (xi) SEQUENCE DESCRIPTION: SEQ ID NO:34:

AGCCATCCTT GGTTCAG                                                  17

(2) INFORMATION FOR SEQ ID NO:35:

(i) SEQUENCE CHARACTERISTICS:
        (A) LENGTH: 15 base pairs
        (B) TYPE: nucleic acid
        (C) STRANDEDNESS: both
        (D) TOPOLOGY: both (xi) SEQUENCE DESCRIPTION: SEQ ID NO:35:

GTAAGGGTGG ATGTT                                                    15

(2) INFORMATION FOR SEQ ID NO:36:

(i) SEQUENCE CHARACTERISTICS:
        (A) LENGTH: 10 amino acids
        (B) TYPE: amino acid
        (D) TOPOLOGY: both (xi) SEQUENCE DESCRIPTION: SEQ ID NO:36:

Met Asp Lys Ser Glu Leu Arg Val Asp Val
1               5                   10

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: both
        (D) TOPOLOGY: both (xi) SEQUENCE DESCRIPTION: SEQ ID NO:37:

ATGGACAAAT CTGAATTAAG GGTGGATGTT                                    30

(2) INFORMATION FOR SEQ ID NO:38:

(i) SEQUENCE CHARACTERISTICS:
        (A) LENGTH: 11 amino acids
        (B) TYPE: amino acid
        (D) TOPOLOGY: both (xi) SEQUENCE DESCRIPTION: SEQ ID NO:38:

Met Glu Asn Phe Ser Ser Tyr His Gly Thr Lys
1               5                   10

(2) INFORMATION FOR SEQ ID NO:39:

(i) SEQUENCE CHARACTERISTICS:
        (A) LENGTH: 70 base pairs
        (B) TYPE: nucleic acid
        (C) STRANDEDNESS: both
        (D) TOPOLOGY: both (xi) SEQUENCE DESCRIPTION: SEQ ID NO:39:

TCTCGATGAT GTTGTTGATT CTTCTAAATC TTTTGTGATT GAAAACTTTT CTTCGTACCA   60

CGGGACTAAA                                                          70

(2) INFORMATION FOR SEQ ID NO:40:

(i) SEQUENCE CHARACTERISTICS:
        (A) LENGTH: 70 base pairs
        (B) TYPE: nucleic acid
        (C) STRANDEDNESS: both
        (D) TOPOLOGY: both (xi) SEQUENCE DESCRIPTION: SEQ ID NO:40:

TCTCGATGAT GTTGTTGATT CTTCTAAATC TTTTGTGTTG GAAAACTTTT CTTCGTACCA        60

CGGGACTAAA        70

(2) INFORMATION FOR SEQ ID NO:41:

(i) SEQUENCE CHARACTERISTICS:
        (A) LENGTH: 41 base pairs
        (B) TYPE: nucleic acid
        (C) STRANDEDNESS: both
        (D) TOPOLOGY: both (xi) SEQUENCE DESCRIPTION: SEQ ID NO:41:

ATGGAGAAAA AAATCACTGG ATATACCACC GTTGATATAT C        41

(2) INFORMATION FOR SEQ ID NO:42:

(i) SEQUENCE CHARACTERISTICS:
        (A) LENGTH: 17 amino acids
        (B) TYPE: amino acid
        (D) TOPOLOGY: both (xi) SEQUENCE DESCRIPTION: SEQ ID NO:42:

Met Glu Lys Lys Ile Thr Asp Ser Leu Ala Val Val Leu Gln Arg Arg
1               5                   10                  15
Asp (2) INFORMATION FOR SEQ ID NO:43:

(i) SEQUENCE CHARACTERISTICS:
        (A) LENGTH: 51 base pairs
        (B) TYPE: nucleic acid
        (C) STRANDEDNESS: both
        (D) TOPOLOGY: both (xi) SEQUENCE DESCRIPTION: SEQ ID NO:43:

ATGGAGAAAA AAATTACGGA TTCACTGGCC GTCGTTTTAC AACGTCGTGA C        51

(2) INFORMATION FOR SEQ ID NO:44:

(i) SEQUENCE CHARACTERISTICS:
        (A) LENGTH: 1038 base pairs
        (B) TYPE: nucleic acid
        (C) STRANDEDNESS: both
        (D) TOPOLOGY: both (xi) SEQUENCE DESCRIPTION: SEQ ID NO:44:

GTCGACCTTT TTAAGTCGGC AAATATCGCA TGTTTGTTCG ATAGACATCG AGTGGCTTCA        60

AAAGTTATCA GGCATGCACC TGGTAGCTAG TCTTTAAACC AATAGATTGC ATCGGTTTAA       120

AAGGCAAGAC CGTCAAATTG CGGGAAAGGG GTCAACAGCC GTTCAGTACC AAGTCTCAGG       180

GGAAACTTTG AGATGGCCTT GCAAAGGGTA TGGTAATAAG CTGACGGACA TGGTCCTAAC       240

CACGCAGCCA AGTCCTAAGT CAACAGATCT TCTGTTGATA TGGATGCAGT TCACAGACTA       300

AATGTCGGTC GGGGAAGATG TATTCTTCTC ATAAGATATA GTCGGACCTC TCCTTAATGG       360

GAGCTAGCGG ATGAAGTGAT GCAACACTGG AGCCGCTGGG AACTAATTTG TATGCGAAAG       420

TATATTGATT AGTTTTGGAG TACTCGTCTC GATGATGTTG TTGATTCTTC TAAATCTTTT       480

```
GTGATTGAAA ACTTTTCTTC GTACCACGGG ACTAAACCTG GTTATGTAGA TTCCATTCAA      540

AAAGGTATAC AAAAGCCAAA ATCTGGTACA CAAGGAAATT ATGACGATGA TTGGAAAGGG      600

TTTTATAGTA CCGACAATAA ATACGACGCT GCGGGATACT CTGTAGATAA TGAAAACCCG      660

CTCTCTGGAA AAGCTGGAGG CGTGGTCAAA GTGACGTATC CAGGACTGAC GAAGGTTCTC      720

GCACTAAAAG TGGATAATGC CGAAACTATT AAGAAAGAGT TAGGTTTAAG TCTCACTGAA      780

CCGTTGATGG AGCAAGTCGG AACGGAAGAG TTTATCAAAA GGTTCGGTGA TGGTGCTTCG      840

CGTGTAGTGC TCAGCCTTCC CTTCGCTGAG GGGAGTTCTA GCGTTGAATA TATTAATAAC      900

TGGGAACAGG CGAAAGCGTT AAGCGTAGAA CTTGAGATTA ATTTTGAAAC CCGTGGAAAA      960

CGTGGCCAAG ATGCGATGTA TGAGTATATG GCTCAAGCCT GTGCAGGAAA TCGTGTCAGG     1020

CGATCTTTGT GACTCGAG                                                   1038

(2) INFORMATION FOR SEQ ID NO:45:

(i) SEQUENCE CHARACTERISTICS:
        (A) LENGTH: 72 base pairs
        (B) TYPE: nucleic acid
        (C) STRANDEDNESS: both
        (D) TOPOLOGY: both (xi) SEQUENCE DESCRIPTION: SEQ ID NO:45:

ATGGAGAAAA AAATCACTGG ATATACCACC GTTGATATAT CCCAATGGCA TCGTAAAGAA       60

CATTTTGAGG CA                                                          72

(2) INFORMATION FOR SEQ ID NO:46:

(i) SEQUENCE CHARACTERISTICS:
        (A) LENGTH: 479 base pairs
        (B) TYPE: nucleic acid
        (C) STRANDEDNESS: both
        (D) TOPOLOGY: both (xi) SEQUENCE DESCRIPTION: SEQ ID NO:46:

AAGCTTCTTT ACGATGCCAT TGGGATATAT CAACGGTGGT ATAAAGCCGT GGTTTTTAAA       60

AGTTATCAGG CATGCACCTG GTAGCTAGTC TTTAAACCAA TAGATTGCAT CGGTTTAAAA      120

GGCAAGACCG TCAAATTGCG GGAAAGGGGT CAACAGCCGT TCAGTACCAA GTCTCAGGGG      180

AAACTTTGAG ATGGCCTTGC AAAGGGTATG GTAATAAGCT GACGGACATG GTCCTAACCA      240

CGCAGCCAAG TCCTAAGTCA ACAGATCTTC TGTTGATATG GATGCAGTAC AGACTAAATG      300

TCGGTCGGGG AAGATGTATT CTTCTCATAA CATATAGTCG GACCTCTCCT TAATGGGAGC      360

TAGCGGATGA AGTGATGCAA CACTGGAGCC GCTGGGAACT AATTTGTATG CGAAAGTATA      420

TTGATTAGTT TTGGAGTACT CGTACGGATT CACTGGCCGT CCTGTTACAA CGTCGTGAC       479

(2) INFORMATION FOR SEQ ID NO:47:

(i) SEQUENCE CHARACTERISTICS:
        (A) LENGTH: 479 base pairs
        (B) TYPE: nucleic acid
        (C) STRANDEDNESS: both
        (D) TOPOLOGY: both (xi) SEQUENCE DESCRIPTION: SEQ ID NO:47:

AAGCTTCTTT ACGATGCCAT TGGGATATAT CAACGGTGGT ATAAAGCCGT GGTTTTTAAA       60

AGTTATCAGG CATGCACCTG GTAGCTAGTC TTTAAACCAA TAGATTGCAT CGGTTTAAAA      120

GGCAAGACCG TCAAATTGCG GGAAAGGGGT CAACAGCCGT TCAGTACCAA GTCTCAGGGG      180

AAACTTTGAG ATGGCCTTGC AAAGGGTATG GTAATAAGCT GACGGACATG GTCCTAACCA      240
```

```
CGCAGCCAAG TCCTAAGTCA ACAGATCTTC TGTTGATATG GATGCAGTAC AGACTAAATG      300

TCGGTCGGGG AAGATGTATT CTTCTCATAA CATATAGTCG GACCTCTCCT TAATGGGAGC      360

TAGCGGATGA AGTGATGCAA CACTGGAGCC GCTGGGAACT AATTTGTATG CGAAAGTATA      420

TTGATTAGTT TTGGAGTACT CGTACGGATT CACTGGCCGT CCTGTTACAA CGTCGTGAC       479

(2) INFORMATION FOR SEQ ID NO:48:

(i) SEQUENCE CHARACTERISTICS:
        (A) LENGTH: 480 base pairs
        (B) TYPE: nucleic acid
        (C) STRANDEDNESS: both
        (D) TOPOLOGY: both (xi) SEQUENCE DESCRIPTION: SEQ ID NO:48:

AAGCTTCTTT ACGATGCCAT TGGGATATAT CAACGGTGGT ATAAAGCCGT GGTTTTTAAA       60

AGTTATCAGG CATGCACCTG GTAGCTAGTC TTTAAACCAA TAGATTGCAT CGGTTTAAAA      120

GGCAAGACCG TCAAATTGCG GGAAAGGGGT CAACAGCCGT TCAGTACCAA GTCTCAGGGG      180

AAACTTTGAG ATGGCCTTGC AAAGGGTATG GTAATAAGCT GACGGACATG GTCCTAACCA      240

CGCAGCCAAG TCCTAAGTCA ACAGATCTTC TGTTGATATG GATGCAGTAC AGACTAAATG      300

TCGGTCGGGA CCGTTGATAT ATGGTTCATA ACATATAGTC GGACCTCTCC TTAATGGGAG      360

CTAGCGGATG AAGTGATGCA ACACTGGAGC CGCTGGGAAC TAATTTGTAT GCGAAAGTAT      420

ATTGATTAGT TTTGGAGTAC TCGTACGGAT TCACTGGCCG TCCTGTTACA ACGTCGTGAC      480

(2) INFORMATION FOR SEQ ID NO:49:

(i) SEQUENCE CHARACTERISTICS:
        (A) LENGTH: 487 base pairs
        (B) TYPE: nucleic acid
        (C) STRANDEDNESS: both
        (D) TOPOLOGY: both (xi) SEQUENCE DESCRIPTION: SEQ ID NO:49:

AAGCTTCTTT ACGATGCCAT TGGGATATAT CAACGGTGGT ATAAAGCCGT GGTTTTTAAA       60

AGTTATCAGG CATGCACCTG GTAGCTAGTC TTTAAACCAA TAGATTGCAT CGGTTTAAAA      120

GGCAAGACCG TCAAATTGCG GGAAAGGGGT CAACAGCCGT TCAGTACCAA GTCTCAGGGG      180

AAACTTTGAG ATGGCCTTGC AAAGGGTATG GTAATAAGCT GACGGACATG GTCCTAACCA      240

CGCAGCCAAG TCCTAAGTCA ACAGATCTTC TGTTGATATG GATGCAGTAC AGACTAAATG      300

TCGGTCGGGA CCGTTGATAT ATCCCAAACG GTTCATAACA TATAGTCGGA CCTCTCCTTA      360

ATGGGAGCTA GCGGATGAAG TGATGCAACA CTGGAGCCGC TGGGAACTAA TTTGTATGCG      420

AAAGTATATT GATTAGTTTT GGAGTACTCG TACGGATTCA CTGGCCGTCC TGTTACAACG      480

TCGTGAC                                                                487

(2) INFORMATION FOR SEQ ID NO:50:

(i) SEQUENCE CHARACTERISTICS:
        (A) LENGTH: 1044 base pairs
        (B) TYPE: nucleic acid
        (C) STRANDEDNESS: both
        (D) TOPOLOGY: both (xi) SEQUENCE DESCRIPTION: SEQ ID NO:50:

GTCGACCTTT TTAAGTCGGC AAATATCGCA TGTTTGTTCG ATAGACATCG AGTGGCTTCA       60

AAAGTTATCA GGCATGCACC TGGTAGCTAG TCTTTAAACC AATAGATTGC ATCGGTTTAA      120
```

| | |
|---|---|
| AAGGCAAGAC CGTCAAATTG CGGGAAAGGG GTCAACAGCC GTTCAGTACC AAGTCTCAGG | 180 |
| GGAAACTTTG AGATGGCCTT GCAAAGGGTA TGGTAATAAG CTGACGGACA TGGTCCTAAC | 240 |
| CACGCAGCCA AGTCCTAAGT CAACAGATCT TCTGTTGATA TGGATGCAGT TCACAGACTA | 300 |
| AATGTCGGTC GGGGAACAAC ATGCGATATT GTTCTCATAA GATATAGTCG GACCTCTCCT | 360 |
| TAATGGGAGC TAGCGGATGA AGTGATGCAA CACTGGAGCC GCTGGGAACT AATTTGTATG | 420 |
| CGAAAGTATA TTGATTAGTT TTGGAGTACT CGTCTCGATG ATGTTGTTGA TTCTTCTAAA | 480 |
| TCTTTTGTGA TTGAAAACTT TTCTTCGTAC CACGGGACTA AACCTGGTTA TGTAGATTCC | 540 |
| ATTCAAAAAG GTATACAAAA GCCAAAATCT GGTACACAAG GAAATTATGA CGATGATTGG | 600 |
| AAAGGGTTTT ATAGTACCGA CAATAAATAC GACGCTGCGG GATACTCTGT AGATAATGAA | 660 |
| AACCCGCTCT CTGGAAAAGC TGGAGGCGTG GTCAAAGTGA CGTATCCAGG ACTGACGAAG | 720 |
| GTTCTCGCAC TAAAAGTGGA TAATGCCGAA ACTATTAAGA AAGAGTTAGG TTTAAGTCTC | 780 |
| ACTGAACCGT TGATGGAGCA AGTCGGAACG GAAGAGTTTA TCAAAAGGTT CGGTGATGGT | 840 |
| GCTTCGCGTG TAGTGCTCAG CCTTCCCTTC GCTGAGGGGA GTTCTAGCGT TGAATATATT | 900 |
| AATAACTGGG AACAGGCGAA AGCGTTAAGC GTAGAACTTG AGATTAATTT TGAAACCCGT | 960 |
| GGAAAACGTG GCCAAGATGC GATGTATGAG TATATGGCTC AAGCCTGTGC AGGAAATCGT | 1020 |
| GTCAGGCGAT CTTTGTGACT CGAG | 1044 |

(2) INFORMATION FOR SEQ ID NO:51:

(i) SEQUENCE CHARACTERISTICS:
        (A) LENGTH: 1047 base pairs
        (B) TYPE: nucleic acid
        (C) STRANDEDNESS: both
        (D) TOPOLOGY: both (xi) SEQUENCE DESCRIPTION: SEQ ID NO:51:

| | |
|---|---|
| GTCGACCTTT TTAAGTCGGC AAATATCGCA TGTTTGTTCG ATAGACATCG AGTGGCTTCA | 60 |
| AAAGTTATCA GGCATGCACC TGGTAGCTAG TCTTTAAACC AATAGATTGC ATCGGTTTAA | 120 |
| AAGGCAAGAC CGTCAAATTG CGGGAAAGGG GTCAACAGCC GTTCAGTACC AAGTCTCAGG | 180 |
| GGAAACTTTG AGATGGCCTT GCAAAGGGTA TGGTAATAAG CTGACGGACA TGGTCCTAAC | 240 |
| CACGCAGCCA AGTCCTAAGT CAACAGATCT TCTGTTGATA TGGATGCAGT TCACAGACTA | 300 |
| AATGTCGGTC GGGCAAACAT GCGATATTTG CCGTTTGTCA TAAGATATAG TCGGACCTCT | 360 |
| CCTTAATGGG AGCTAGCGGA TGAAGTGATG CAACACTGGA GCCGCTGGGA ACTAATTTGT | 420 |
| ATGCGAAAGT ATATTGATTA GTTTTGGAGT ACTCGTCTCG ATGATGTTGT TGATTCTTCT | 480 |
| AAATCTTTTG TGATTGAAAA CTTTTCTTCG TACCACGGGA CTAAACCTGG TTATGTAGAT | 540 |
| TCCATTCAAA AAGGTATACA AAAGCCAAAA TCTGGTACAC AAGGAAATTA TGACGATGAT | 600 |
| TGGAAAGGGT TTTATAGTAC CGACAATAAA TACGACGCTG CGGGATACTC TGTAGATAAT | 660 |
| GAAAACCCGC TCTCTGGAAA AGCTGGAGGC GTGGTCAAAG TGACGTATCC AGGACTGACG | 720 |
| AAGGTTCTCG CACTAAAAGT GGATAATGCC GAAACTATTA AGAAAGAGTT AGGTTTAAGT | 780 |
| CTCACTGAAC CGTTGATGGA GCAAGTCGGA ACGGAAGAGT TTATCAAAAG GTTCGGTGAT | 840 |
| GGTGCTTCGC GTGTAGTGCT CAGCCTTCCC TTCGCTGAGG GGAGTTCTAG CGTTGAATAT | 900 |
| ATTAATAACT GGGAACAGGC GAAAGCGTTA AGCGTAGAAC TTGAGATTAA TTTTGAAACC | 960 |
| CGTGGAAAAC GTGGCCAAGA TGCGATGTAT GAGTATATGG CTCAAGCCTG TGCAGGAAAT | 1020 |
| CGTGTCAGGC GATCTTTGTG ACTCGAG | 1047 |